(12) United States Patent
Myerson et al.

(10) Patent No.: US 9,233,912 B2
(45) Date of Patent: Jan. 12, 2016

(54) DEVICES AND METHODS FOR CRYSTALLIZATION

(71) Applicant: Massachusetts Institute of Technology, Cambridge, MA (US)

(72) Inventors: Allan Stuart Myerson, Boston, MA (US); Shin Yee Wong, Cambridge, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 14/174,355

(22) Filed: Feb. 6, 2014

(65) Prior Publication Data
US 2014/0256984 A1  Sep. 11, 2014

Related U.S. Application Data

(60) Provisional application No. 61/761,659, filed on Feb. 6, 2013.

(51) Int. Cl.
*C07C 227/42* (2006.01)
*C07C 231/22* (2006.01)
*B01D 9/00* (2006.01)

(52) U.S. Cl.
CPC ............ *C07C 227/42* (2013.01); *B01D 9/0036* (2013.01); *B01D 9/0063* (2013.01); *B01D 9/0072* (2013.01); *C07C 231/22* (2013.01)

(58) Field of Classification Search
CPC .............................. C30B 35/00; C30B 35/002
USPC .......................... 117/202; 435/239
See application file for complete search history.

(56) References Cited

U.S. PATENT DOCUMENTS

2001/0006807 A1* 7/2001 Bray et al. .................... 435/239
2011/0203515 A1* 8/2011 Krautter .......................... 117/69

OTHER PUBLICATIONS

Jones, Crystal formation and breakage. In:Crystallization Process Systems. 2002. Butterworth-Heinemann. Oxford. Chapter 5:123-154.
Ten Wolde et al., Enhancement of protein crystal nucleation by critical density fluctuations. Science. Sep. 26, 1997;277(5334):1975-8.
[No Author Listed] ACR 100 Operating instructions. Coflore. AM Technology Engineering Chemistry. 2011.
Alvarez et al., Crystallization of Cyclosporine in a Multistage Continuous MSMPR Crystallizer. Cryst. Growth Des. 2011;11(10):4392-4400.
Denk et al., Mechanism of contact nucleation. J Cryst Growth. 1972;15(1):57-60.
Erdemir et al., Nucleation of crystals from solution: classical and two-step models. Acc Chem Res. May 19, 2009;42(5):621-9. doi: 10.1021/ar800217x.
Garside et al., Direct observation of secondary nuclei production. J Crystal Growth. 1978;43:694-704.
Garside et al., Secondary contact nucleation: kinetics, growth and scale-up. Chem Eng Commun. 1980;4:393-424.
Holden, Growing single crystals from solution. Discuss. Faraday Soc. 1949;5:312-315.
Kirwan et al., Crystallization in the pharmaceutical and bioprocessing industries. Handbook Industrial Crystallization. Second edition. 2002;249-266.
Lal et al., Collision breeding of crystal nuclei. J Cryst Growth. Feb. 1969;5(1):1-8.
Myerson et al., Crystals, crystal growth and nucleation. Handbook of Industrial Crystallization. $2^{nd}$ edition. Butterworth-Heinemann: Woburn. 2002. 33-65.
Nicolis et al., Enhancement of the nucleation of protein crystals by the presence of an intermediate phase: a kinetic model. Physica A. May 2003;323:139-154.
Pieter et al., Enhancement of Protein Crystal Nucleation by Critical Density Fluctuations. Science. Sep. 1997. 277:1975-1978.
Tai et al., Contact nucleation of various crystal types. AIChE J. Mar. 1975;21(2):351-358.
Vekilov, Two-step mechanism for the nucleation of crystals from solution. J Crys Growth. Feb. 2005;275:65-76.
Wissing et al., In situ observation of secondary nucleation. J Cryst Growth. Dec. 1986;79(1-3):614-619.

* cited by examiner

*Primary Examiner* — Yong Chu
(74) *Attorney, Agent, or Firm* — Wolf, Greenfield & Sacks, P.C.

(57) ABSTRACT

The invention in some aspects relates to devices and methods for nucleating crystals under controlled conditions. In some aspects of the invention, devices and methods are provided for continuous crystallization.

9 Claims, 16 Drawing Sheets

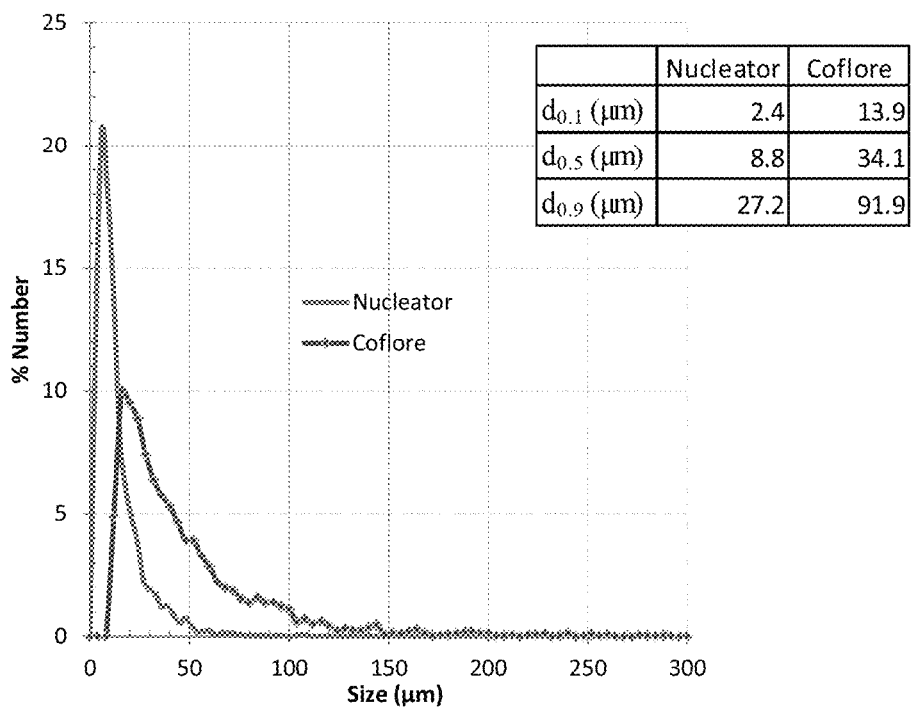
FIG. 10
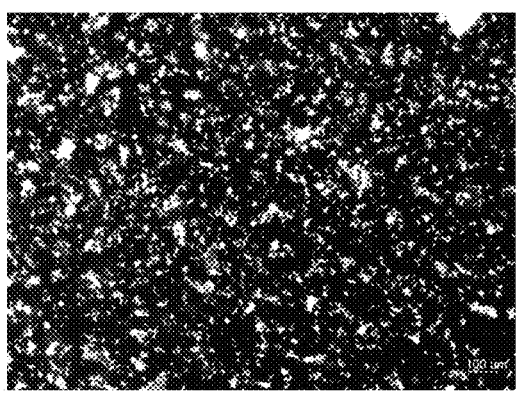
FIG. 11A   Nucleator
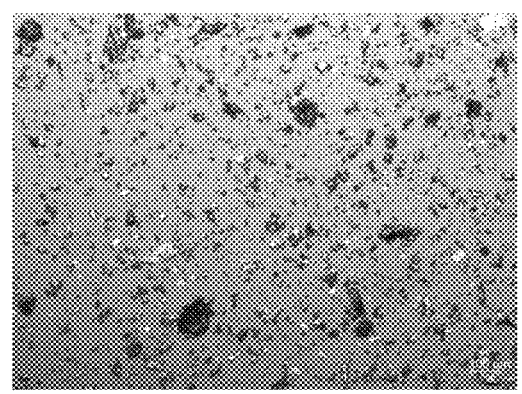
FIG. 11B   Coflore crystallizer

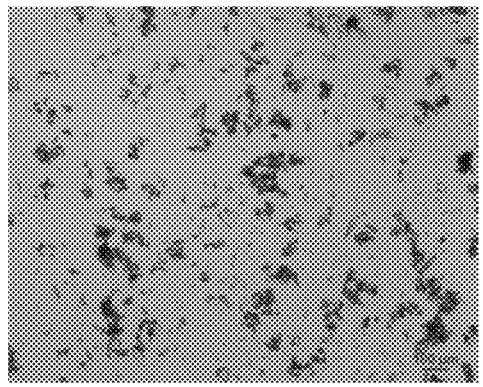
FIG. 15A   Seed crystal
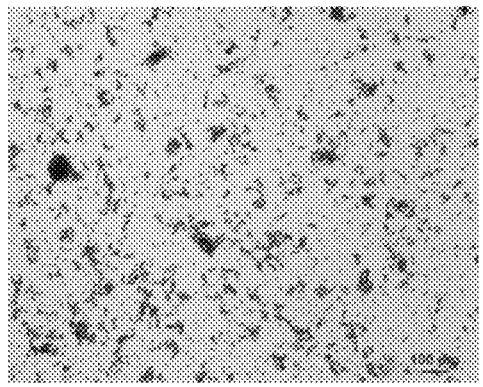
FIG. 15B Coflore crystallizer
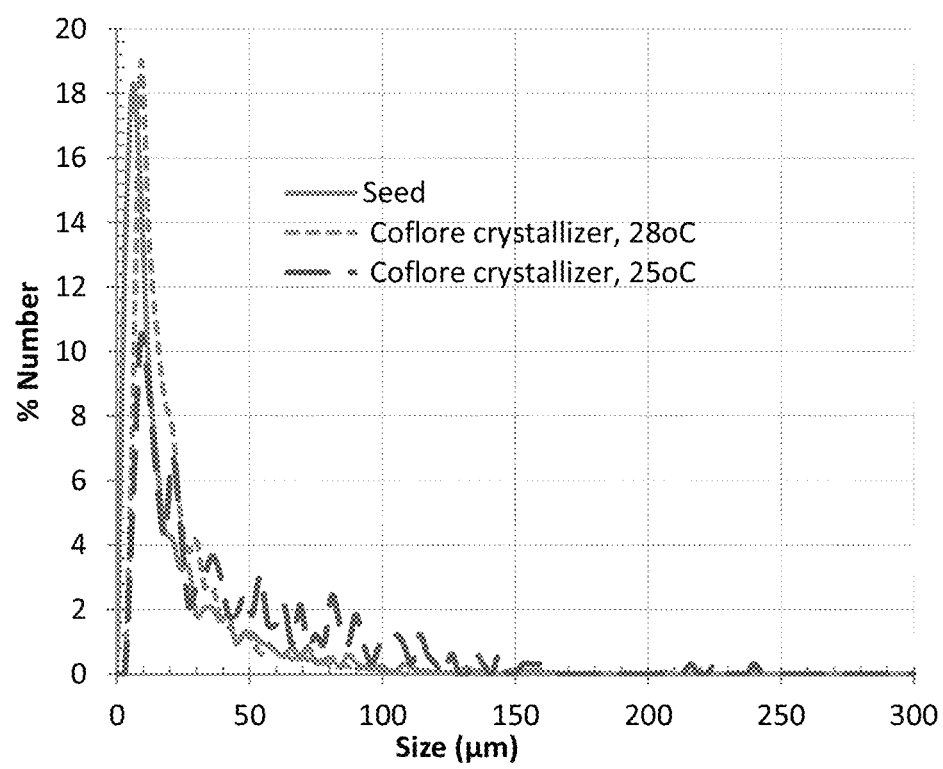
FIG. 16

US 9,233,912 B2

DEVICES AND METHODS FOR CRYSTALLIZATION

RELATED APPLICATIONS

This application claims priority under 35 U.S.C. §119(e) to U.S. Provisional Application Ser. No. 61/761,659, entitled "DEVICES AND METHODS FOR CRYSTALLIZATION" filed on Feb. 6, 2013, which is herein incorporated by reference in its entirety.

BACKGROUND OF INVENTION

In industries such as the chemical, pharmaceutical, and food industries, crystallization from solution is widely used to produce a variety of materials. In the pharmaceutical industry, for example, controlled crystallization processes are important for producing desired crystal forms and sizes that assures appropriate bioavailability and stability of the drug substance. Hence it is advantageous to control the crystallization process in order to obtain products with desired and reproducible properties. To produce small crystals with narrow size distribution, antisolvent crystallization has often been used. Traditional antisolvent crystallization systems often utilize rapid mixing of solution and antisolvent, and employ devices designed to eliminate local regions of uncontrolled supersaturation, e.g., impinging jets, tee-mixers, and static mixers. Unfortunately, these systems are often unsuitable for producing appropriate crystals for particular applications, and are limited in that they often require high supersaturation to trigger nucleation.

SUMMARY OF INVENTION

Disclosed are devices and methods for producing crystals under controlled conditions. In some embodiments, devices and methods provided are useful for producing crystals in a wide range of settings including the chemical, pharmaceutical, and food industries. In some embodiments, devices and methods provided are useful for producing crystals of a desired size range under controlled conditions. In some embodiments, methods involve controlling the balance between crystal nucleation and growth processes, such that the size distribution of the crystals can be manipulated during the crystallization process, leading to the production of crystals of desired sizes. In some embodiments, devices and methods provided are useful for producing crystals of relatively small sizes. In certain such embodiments, the devices and methods are useful in the pharmaceutical industry and related industries where small crystal sizes are often desirable (e.g., for producing drug substances having improved pharmacokinetics or pharmacodynamics, including, e.g., dissolution rate and/or bioavailability). In some embodiments, devices and methods are provided that are useful for producing crystals comprising active pharmaceutical ingredients. In some embodiments, devices and methods provided herein allow for crystals of relatively uniform size to be produced without additional post-processing e.g., milling.

According to some aspects, methods are provided for processing crystals. In some embodiments, the methods comprise: (a) supplying a crystallizer with crystals having a first characteristic size; (b) maintaining the crystallizer under conditions suitable for growth of the crystals supplied to the crystallizer; (c) recovering from the crystallizer crystals having a second characteristic size; and (d) controlling the extent of growth of crystals supplied to the crystallizer by controlling rate at which crystals are supplied to and recovered from the crystallizer, wherein the difference between the first characteristic size and the second characteristic size is indicative of the extent of growth of crystals supplied to the crystallizer. In some embodiments, step (a) comprises supplying the crystallizer continuously or substantially continuously over a period of time, with crystals having a first characteristic size. In some embodiments, step (a) comprises supplying the crystallizer with the crystals on multiple occasions during a single operation.

In some embodiments, the methods further comprise producing the crystals that are fed to the crystallizer. In some embodiments, crystals that are fed to the crystallizer are produced through a secondary nucleation process. In some embodiments, a secondary nucleation process comprises: combining a supersaturated solution with a parent crystal in a nucleation chamber, wherein both the supersaturated solution and the parent crystal comprise constituents of the crystals to be produced; and applying a mechanical force to the parent crystal while the supersaturated solution is exposed to a parent crystal. In certain embodiments, the mechanical force is a fluid shear force, an impact force or a frictional force. In certain embodiments, the mechanical force is a frictional force. In some embodiments, the concentration of the constituents in the supersaturated solution remains within the metastable zone width of the constituents. In some embodiments, the secondary nucleation process further comprises producing the crystals having the first characteristic size, at least in part, by controlling the magnitude of the applied mechanical force. In certain embodiments, the methods further comprise monitoring the magnitude of the applied mechanical force (e.g., through the use of a force gauge configured for measuring the applied mechanical force). In some embodiments, the parent crystal is immobilized in the nucleation chamber, and the supersaturated solution is contacted with the parent crystal in the nucleation chamber by flowing the supersaturated solution through the nucleation chamber. In some embodiments, the secondary nucleation process further comprises producing the crystals having the first characteristic size, at least in part, by controlling the residence time of the supersaturated solution in the nucleation chamber.

In some embodiments, the residence time of the supersaturated solution in the nucleation chamber is up to 1 minute or up to 3.5 minutes or more or less depending on the volume of the nucleation chamber and flow rate of the fluid through the chamber and desired extent of nucleation. In some embodiments, the secondary nucleation process further comprises producing the crystals having the first characteristic size, at least in part, by controlling the flow rate of the supersaturated solution through the nucleation chamber. In some embodiments, the secondary nucleation process further comprises producing the crystals having the first characteristic size, at least in part, by controlling the concentration of constituents in supersaturated solution.

In some embodiments, the methods further comprise controlling the extent of crystal growth in the crystallizer by controlling the temperature within the crystallizer. In some embodiments, the extent of crystal growth in a crystallizer depends, at least in part, on the residence time of the crystals in the crystallizer. Thus, in some embodiments, the methods further comprise controlling the residence time of the crystals in the crystallizer by controlling the feed rate into the crystallizer and the recovery rate from the crystallizer. In some embodiments, the methods further comprise controlling the residence time of the crystals in the crystallizer by controlling the volume of medium comprising the crystals in the crystallizer. In certain embodiments, the residence time of the crystals in the crystallizer is up to 5 minutes. In certain embodiments, the residence time of the crystals in the crystallizer is in a range of 1 to 3 minutes, or more or less depending on the volume of the crystallizer and flow rate of the fluid containing the crystals and desired growth. In certain embodiments, the crystallizer is a plug-flow crystallizer, a stirred tank crystallizer or a micro-crystallizer.

In some embodiments, the first characteristic size is a mean chord length of crystals of up to 25 µm, and the second characteristic size is a mean chord length of crystals in a range of above 25 to 75 µm. In some embodiments, the first characteristic size is at least 80% of the crystals having a mean chord length in a range of 1 to 35 µm, and the second characteristic size is at least 80% of the crystals having a mean chord length in a range of 10 to 95 µm.

According to some aspects, methods for crystallization are provided that comprise: (a) producing crystals by inducing contact nucleation of a parent crystal; (b) supplying a crystallizer with the crystals produced in step (a); (c) maintaining the crystallizer under conditions suitable for growth of crystals supplied to the crystallizer; and (d) recovering crystals from the crystallizer, wherein the recovered crystals comprise crystals produced in step (a) that have grown in the crystallizer. In some embodiments, step (b) comprises supplying the crystallizer with the crystals continuously or substantially continuously for a period of time. In some embodiments, step (a) comprises supplying the crystallizer with the crystals on multiple occasions during a single operation. In some embodiments, the parent crystal is a compression tablet.

According to some aspects, methods for crystallization are provided that comprise: (a) producing crystals through contact nucleation of a parent crystal, wherein the parent crystal is a compression tablet; (b) feeding a crystallizer with the crystals; and (c) maintaining the crystallizer under conditions suitable for growth of the crystals.

According to some aspects, methods for crystallization are provided that comprise: (a) providing a first housing, the first housing comprising a nucleation chamber, the nucleation chamber being configured such that when a supersaturated solution is present in the nucleation chamber contact nucleation occurs resulting in the formation of crystals; (b) providing a second housing, the second housing comprising a crystallization chamber, the crystallization chamber being configured to support growth of the crystals; (c) supplying a supersaturated solution to the nucleation chamber such that contact nucleation occurs resulting in the formation of crystals in the nucleation chamber; (d) controlling the extent of formation of crystals in the nucleation chamber by controlling the residence time of the supersaturated solution in the nucleation chamber; (e) transferring the crystals from the nucleation chamber to the crystallizer chamber; and (f) controlling the extent of growth of the crystals in the crystallization chamber by controlling the residence time of the crystals in the crystallization chamber. In some embodiments, step (e) comprises transferring the crystals to the crystallization chamber through a fluid flow path that connects the nucleation chamber and the crystallization chamber. In some embodiments, a parent crystal is present in a nucleation chamber, and the methods further comprises applying a mechanical force to the parent crystal while the supersaturated solution is present in the nucleation chamber, wherein the contact nucleation occurs at least in part as a result of the applied mechanical force.

According to some aspects, methods for crystallization are provided that comprise: contacting a supersaturated solution with a parent crystal in a nucleation chamber, wherein both the supersaturated solution and the parent crystal comprise constituents of the crystals to be produced, and wherein the parent crystal is a compression tablet; and applying a mechanical force to the parent crystal while the supersaturated solution is exposed to a parent crystal.

According to some aspects, devices are provided for nucleating crystals. In some embodiments, the device for nucleating crystals comprises a housing that comprises a nucleation chamber, a fluid inlet and a fluid outlet, the fluid inlet and fluid outlet each being in fluid communication with the nucleation chamber; a parent crystal connected to a support member within the nucleation chamber; and a motive device configured for generating relative tangential motion between the parent crystal and a contact surface within the nucleation chamber, such that a frictional force is generated between the parent crystal and the contact surface. In some embodiments, the device is configured such that, when a supersaturated solution comprising the same compounds that are constituents of the parent crystal is present in the nucleation chamber while the relative tangential motion is generated, a population of crystals comprising the compounds is produced in the nucleation chamber. In some embodiments, 80% of the crystals in the population have a mean chord length in a range of 1 to 35 µm. In some embodiments, the parent crystal and the contact surface are configured such that a substantially normal force is exerted on the parent crystal through the contact surface. In some embodiments, the substantially normal force is in a range of 0.01 N to 25 N. In some embodiments, the motive device is configured for generating the relative tangential motion by applying a force to the support member. In some embodiments, the support member extends through a passage in the housing and comprises a distal end disposed within the nucleation chamber and a proximal end disposed outside of the housing. In some embodiments, the motive device is coupled to the proximal end of the support member. In some embodiments, the parent crystal is connected to the distal end of the support member. In some embodiments, the motive device is an electromotive device (e.g., an electric motor). In some embodiments, the motive device is configured for rotating the support member relative to the contact surface to produce the relative tangential motion between the parent crystal and a contact surface. In some embodiments, the motive device is configured for translating the support member relative to the contact surface to produce the relative tangential motion between the parent crystal and a contact surface. In some embodiments, the parent crystal has a mean chord length or diameter in a range of 500 µm to 5 mm. In some embodiments, the parent crystal comprises a pharmaceutical compound. In some embodiments, the parent crystal is a compression tablet.

According to some aspects, methods of nucleating crystals are provided that comprise (i.) obtaining any of the crystal nucleation devices disclosed herein; (ii.) causing the motive device of the nucleation device to generate relative tangential motion between the parent crystal and a contact surface within the nucleation chamber, such that a frictional force is generated between the parent crystal and the contact surface; and (iii.) transferring a solution to the nucleation chamber, wherein the solution comprises the same compounds that are constituents of the parent crystal that is present in the nucleation chamber, such that crystals comprising the compounds are produced in the nucleation chamber while the frictional force is generated between the parent crystal and the contact surface.

In some embodiments, a device for nucleating crystals comprises a housing that comprises a nucleation chamber; a parent crystal connected to a support member within the nucleation chamber; and a motive device connected to the housing and configured for generating a mechanical force between the parent crystal and the contact surface; and a controller configured to automatically control the magnitude of the mechanical force by controlling operation of the motive device and/or by controlling the extent of a compression force exerted between the parent crystal and the contact surface.

In some embodiments, a device for nucleating crystals comprises a housing that comprises a nucleation chamber; a parent crystal connected to a support member within the nucleation chamber, wherein the parent crystal is a compression tablet; and a motive device connected to the housing and configured for generating a mechanical force between the parent crystal and the contact surface.

According to some aspects, devices for processing crystals are provided that comprise (i.) a crystal nucleation device; (ii.) a first container comprising a fluid outlet fluidically connected with a fluid inlet of the housing of the nucleation device; (iii.) a second container comprising a fluid inlet fluidically connected with a fluid outlet of the housing of the nucleation device; and (iv.) at least one fluid transfer device configured for transferring fluid from the first container through the nucleation chamber of the nucleation device to the second container. In some embodiments, the at least one fluid transfer device is positioned between the fluid outlet of the storage container and the fluid inlet of the housing, and is configured for transferring fluid from the first container to the nucleation chamber of the device. In some embodiments, the at least one fluid transfer device is positioned between the fluid outlet of the housing and the fluid inlet of the second container, and is configured for transferring fluid from the nucleation chamber of the device to the second container. In some embodiments, the first container is configured to contain a supersaturated solution comprising the same compounds that are constituents of the parent crystal under conditions that maintain the solution in its supersaturated state. In some embodiments, the second chamber is configured for containing a solution comprising crystals produced in the nucleation chamber under conditions that promote growth of the crystals. In some embodiments, the at least one fluid transfer device is configured for drawing fluid out from the second container, such that the residence time of the growing crystals in the second container is determined by the volume of the second container and the flow rate out from the second container. In some embodiments, the flow rate of fluid being drawn out from the second container is substantially the same as the flow rate of fluid entering the second container from the nucleation chamber.

In some embodiments, methods are provided that comprise obtaining a device for processing crystals that comprises (i.) a crystal nucleation device; (ii.) a first container comprising a fluid outlet fluidically connected with a fluid inlet of the housing of the nucleation device; (iii.) a second container comprising a fluid inlet fluidically connected with a fluid outlet of the housing of the nucleation device; and (iv.) at least one fluid transfer device configured for transferring fluid from the first container through the nucleation chamber of the nucleation device to the second container. In some embodiments, the methods further comprise producing crystals in a crystal nucleation device; transferring the crystals to the second container; and growing the crystals in the second container. In some embodiments, the methods comprise causing the motive device of the nucleation device to generate relative tangential motion between the parent crystal and a contact surface within the nucleation chamber, such that a frictional force is generated between the parent crystal and the contact surface; and transferring a solution to the nucleation chamber, wherein the solution comprises the same compounds that are constituents of the parent crystal that is present in the nucleation chamber, such that crystals comprising the compounds are produced in the nucleation chamber while the frictional force is generated between the parent crystal and the contact surface. In some embodiments, the methods further comprise drawing fluid out from the second container, such that the residence time of the growing crystals in the second container is determined by the volume of the second container and the flow rate out from the second container.

BRIEF DESCRIPTION OF DRAWINGS

FIG. 10 shows size distribution plots of glycine crystals obtained from an integrated nucleator-crystallizer;

FIGS. 11A and 11B are microscopic images of glycine crystals from an integrated nucleator-crystallizer, showing in (A) crystals from nucleator and in (B) crystals from a Coflore crystallizer;

FIGS. 15A and 15B are microscopic images for the glycine crystals obtained from a continuous crystallization process with seeding, showing in (A) nuclei and in (B) crystals from Coflore crystallizer; and FIG. 16. shows crystal size distribution plots of from a continuous crystallization process (crystallizer held at 28 and 25° C., respectively).

DETAILED DESCRIPTION OF INVENTION

Figure 1A:
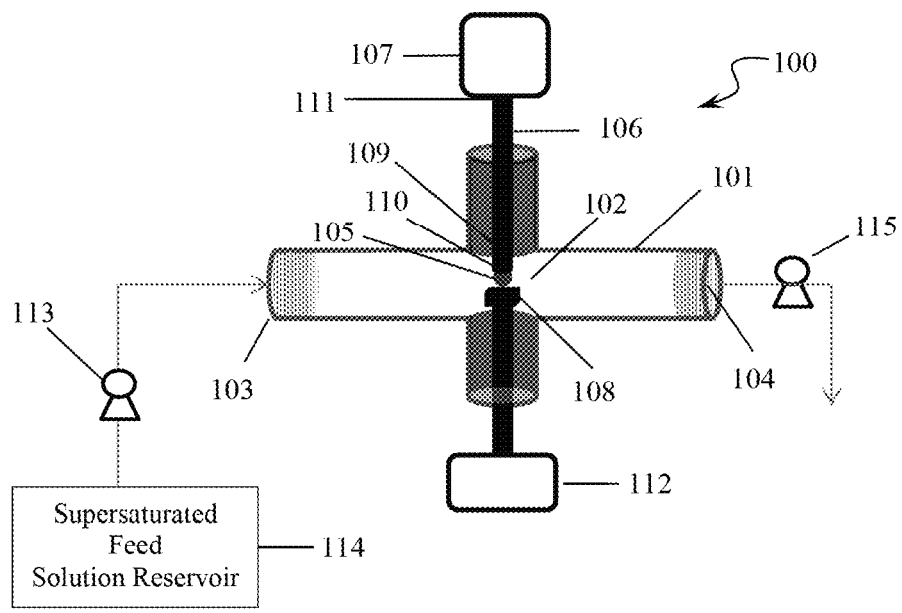
FIGS. 1A, 1B, 1C, and 1D are schematic diagrams of nuclei generator (nucleator)

Disclosed are devices and methods for producing populations of crystals under controlled conditions. In certain industries, it has been difficult to produce crystals of proper structure having an appropriate size distribution using conventional crystallization techniques, especially if very small sizes are desired. Described are devices and methods for nucleating populations of crystals that have relatively small sizes and relatively narrow size distributions. In some embodiments, devices and methods described herein facilitate continuous, semi-continuous or batch processing of crystals to produce crystals of a desired size distribution.

In some embodiments, crystallization from solution involves a two-step process of nucleation and crystal growth. In some embodiments, nucleation involves the creation or "birth" of new crystals (nuclei). In certain embodiments, once created, these nuclei can grow to larger sizes during a growth step, in which particles are transported (e.g. by convection and/or diffusion) to the surface of the nuclei to be incorporated into a crystal lattice.

In some embodiments, nucleation may be classified as primary or secondary nucleation. In some embodiments, primary nucleation occurs in the absence of crystalline surfaces. In some embodiments, secondary nucleation occurs in the presence of parent crystals that interact with the environment (e.g., other crystals, crystallizer walls, impeller, etc.) to generate new crystals. In some embodiments, nucleation may involve solute molecules combining in a series of bi-molecular reactions to produce ordered aggregates. However, in some embodiments, nucleation may involve formation of sufficient-sized clusters of solute molecules, followed by reorganization of the clusters into ordered structures.

In some embodiments, primary nucleation mechanisms are advantageous in precipitation processes and for crystallization in regions of high local supersaturation. However, in some embodiments, crystallization occurring at lower supersaturation level involves primarily secondary nucleation (e.g., contact nucleation). In some embodiments, contact nucleation also produces many times more nuclei than other types of secondary nucleation.

As used herein the term, "nucleation device" refers to a device within which nucleation occurs under controlled conditions. In some embodiments, a nucleation device is referred to as a "nucleator." In some embodiments, nucleation occurring in a nucleation device is primarily secondary nucleation. In some embodiments, nucleation occurring in a nucleation device is primarily secondary contact nucleation. However, in some embodiments, nucleation occurring in the nucleation device involves primary nucleation. In some embodiments, crystals produced in a nucleator, e.g., through contact nucleation, may be referred to as "nuclei" or "seed crystals."

As used herein the term, "crystallization device" refers to a device within which growth of crystals or nuclei (e.g., nuclei from a nucleator) occurs under controlled conditions. In some embodiments, a crystallization device is referred to as a "crystallizer."

In some embodiments, devices are provided that are capable of producing uniformly sized or substantially uniformly sized crystals in a rapid manner. In some embodiments, the methods involve decoupling nucleation and growth events into separate domains (e.g., physical domains, temporal domains, or both), and thereby, allowing advantageous control of each individual event. In some embodiments, once small crystals are generated in a nucleation device, the resulting crystal slurry can be directed from the device into a downstream crystallizer (e.g., plug flow crystallizer, stirred tank crystallizer, micro-crystallizer, microfluidics crystallizer, tubular crystallizer, etc.) for further growth of crystals into larger sizes.

In some embodiments, devices and methods provided facilitate continuous processing of crystals to produce crystals of a desired size distribution. In some embodiments, processing of crystals using certain embodiments of the methods and devices herein involves nucleation and growth of crystals within a continuous or substantially continuous flow process. For example, in some embodiments, a supersaturated solution is continuously (without substantial interruption for an extended period of time) fed through a nucleation device. In some embodiments, a supersaturated solution is fed through a nucleation device without substantial interruptions over a period of at least 30 minutes, at least 1 hour, at least 2 hours, at least 6 hours, at least 12 hours, at least 24 hours, at least 36 hours, at least 48 hours, at least 72 hours, or at least one week. In some embodiments, a supersaturated solution is fed through a nucleation device without substantial interruptions over a period in a range of 30 minutes to 1 hour, 30 minutes to 6 hours, 1 hour to 12 hours, 6 hours to 24 hours, 6 hours to 36 hours, 12 hours to 48 hours, 12 hours to 72 hours, 12 hours to 96 hours, 12 hours to 120 hours, 12 hours to 1 week or 24 hours to 1 month, or longer.

It should be appreciated that while a supersaturated solution is fed (e.g., continuously fed) through a nucleation device the residence time within the device will depend at least in part on the flow rate through the device and the fluid capacity of the device.

In some embodiments, crystals are nucleated in the nucleation device through secondary nucleation. In some embodiments, crystals are nucleated in the nucleation device through contact nucleation. In some embodiments, crystals are nucleated in the nucleation device as a result of exposure of the supersaturated solution to one or more primary crystals located within the device.

In some embodiments, crystals nucleated in the nucleation device are continuously or substantially continuously transferred (e.g., delivered as a slurry of crystals suspended in solution) to and through a crystallizer, which is maintained under conditions suitable for crystal growth, and the crystals grow as they pass through crystallizer. In some embodiments, crystals nucleated in the nucleation device are transferred to and through a crystallizer without substantial interruptions over a period of at least 30 minutes, at least 1 hour, at least 2 hours, at least 6 hours, at least 12 hours, at least 24 hours, at least 36 hours, at least 48 hours, at least 72 hours, at least 96 hours, at least 120 hours, or at least 1 week, or longer. In some embodiments, crystals nucleated in the nucleation device are transferred to and through a crystallizer without substantial interruptions over a period in a range of 30 minutes to 1 hour, 30 minutes to 6 hours, 1 hour to 12 hours, 6 hours to 24 hours, 6 hours to 36 hours, 12 hours to 48 hours, 12 hours to 72 hours, 12 hours to 96 hours, 12 hours to 120 hours, 12 hours to 1 week or 24 hours to 1 month, or longer.

It should be appreciated that while a supersaturated solution is fed (e.g., continuously fed) through a crystallizer the residence time within the crystallizer will depend at least in part on the flow rate through the crystallizer and the fluid capacity of the crystallizer.

In some embodiments, the crystals are continuously or substantially continuously recovered from the crystallizer. In some embodiments, a continuous flow of fluid is maintained (e.g., at a substantially constant flow rate) through the nucleation device and the crystallizer. In some embodiments, a continuous flow of fluid is maintained (e.g., at a substantially constant flow rate) through the nucleation device and the crystallizer such that the rate of nucleation in the nucleation device and the extent of crystal growth in the crystallizer reach steady states.

It should be appreciated that in some embodiments one or more aspects of a process may be implemented in a batch or semi-continuous mode to produced crystals of a desired size distribution. For example, in some embodiments, crystals nucleated in a nucleation device may be intermittently fed to a crystallizer. In some embodiments, crystals nucleated in a nucleation device may be transfer to a crystallizer over the course of multiple distinct periods of time between which periods of time crystals are not transferred to the crystallizer. In some embodiments, crystals nucleated in the nucleation device may be collected and fed in one or more batches to a crystallizer. Similarly, in some embodiments, crystals may be recovered from a crystallizer intermittently, as one or more batches, or over the course of one or more distinct periods of time.

In some embodiments, flow rates through the nucleation device and crystallizer may be substantially the same. In some embodiments, flow rates through the nucleation device and crystallizer may be different. For example, in some embodiments, flow rates through a nucleation device and crystallizer may be independently controlled and/or maintained to achieved desired rates of nucleation and crystal growth in the nucleation device and crystallizer, respectively.

In some embodiments, nucleators are provided that comprise a crossed flow tube with multiple openings (e.g., four openings), such as is depicted in FIG. 1. In some embodiments, the openings include an inlet configured to permit entry of a supersaturated solution into the nucleator, and an outlet configured to permit exit of a nuclei slurry out from the nucleator. In some embodiments, nucleators are provided that are configured such that contact nucleation occurs at least in part as a result of a force (e.g., frictional force, compressive force) being generated between a parent crystal and a rigid platform in the presence of a supersaturated solution comprising constituents of the crystal. In some embodiments, the rate of nucleation and size of crystals generated by nucleators provided herein is controlled by controlling process parameters, such as extent of supersaturation of a feed solution, temperature of the solution within the nucleator, magnitude of force generated between parent crystal and contact platform, and/or residence time in the nucleator.

In some embodiments, devices and methods are provided for generating uniformly or substantially uniformly sized crystals in continuous flow processes. In some embodiments, nucleators are provided that generate small nuclei continuously as a result of pressure being exerted (e.g., cyclically) between a parent crystal and a contact platform. In such embodiments, size of secondary nuclei produced is manipulated by controlling process parameters, such as, for example, supersaturation of a feed solution (e.g., supersaturated solution) in the nucleator, residence time (flow rate) of the solution in the nucleator, temperature of the nucleator, etc.

An exemplary embodiment of a nucleation device according to the invention is depicted in FIG. 1. The device, which is configured for facilitating secondary nucleation, comprises a housing 101 that comprises a nucleation chamber 102, a fluid inlet 103 and a fluid outlet 104. The fluid inlet 103 and fluid outlet 104 are in fluid communication with the nucleation chamber 102. The device is configured with a parent crystal 105 connected to a support member 106 within the nucleation chamber 102. A motive device 107 is provides and is configured for generating relative tangential motion between the parent crystal 105 and a contact surface 108 within the nucleation chamber 102, such that a frictional force is generated between the parent crystal 105 and the contact surface 108. In some embodiments, the device 100 is configured such that, if a supersaturated solution comprising the same compounds that are constituents of the parent crystal 105 is present in the nucleation chamber 102 while the relative tangential motion is generated by the motive device 107, a population of nuclei comprising the compounds is produced in the nucleation chamber 102.

The device may be further configured with a force gauge for measuring force (e.g., compression force) generated between the parent crystal 105 and contact surface 108. The device may be configured with a digital force gauge, for example, that is configured to communicate with a controller that controls the magnitude of the applied force between the parent crystal 105 and contact surface 108. In some embodiments, the size of the crystals produced in the nucleator can be controlled by controlling the magnitude of the applied force. In some embodiments, the device is configured such that a normal force is exerted on the parent crystal 105 through the contact surface 108. The normal force may be in a range of 0.01 N to 25 N, 0.01 N to 10 N, 0.01 N to 5 N, 0.1 N to 100 N, 0.1 N to 50 N, 0.1 N to 5 N, 1 N to 50 N, or 1 N to 5 N, for example.

Moreover, the motive device 107 may be configured, in some embodiments, for generating the relative tangential motion by transmitting a force (e.g., a rotational force) via a support member 106. In some embodiments, the support member 106 extends through a passage 109 in the housing 101 and comprises a distal end 110 disposed within the nucleation chamber 102 and a proximal end 111 disposed outside of the housing 101. In some embodiments, the motive device 107 is coupled to the proximal end 111 of the support member 109. And, in some embodiments, the parent crystal 105 is connected to the distal end 110 of the support member 106. In some embodiments, parent crystal 105 is compressed against contact surface 108 by the weight of support member 106 and motive device 107. In some embodiments, additional weights may be added (e.g., by connecting the weights to the support member) to increase the magnitude of the compressive force applied to the parent crystal 105. In some embodiments, the motive device 107 is an electromotive device (e.g., an electric motor). The motive device 107, in some embodiments, is configured for rotating the support member 106 relative to the contact surface 108. In some embodiments, the motive device 107 is configured for translating the support member 109 relative to the contact surface 108. As the motive device 107 generates tangential motion or translational motion a frictional force is generated between the parent crystal 105 and the contact surface 108 that is proportional to the magnitude of the compressive force applied to the parent crystal 105 through the support member 106 and contact surface 108.

In some embodiments, operation of the nucleation device 100 involves causing the motive device 107 to generate relative tangential motion between the parent crystal 105 and a contact surface 108 within the nucleation chamber 102, such that a frictional force is generated between the parent crystal 105 and the contact surface 108; and transferring a solution to the nucleation chamber 102, e.g., from a storage container 114 containing a feed solution. The solution may be transferred to the nucleator from the storage container 114 to the inlet 103 of the nucleation chamber 102 using a fluid transfer device 113 (e.g., a pump, a peristaltic pump) positioned in fluid communication between the storage container 114 and the inlet 103. Generally, the feed solution comprises the same compounds that are constituents of the parent crystal 105 that is present in the nucleation chamber 102, such that seed crystals (nuclei) comprising the compounds are produced in the nucleation chamber 102 while the frictional force is generated between the parent crystal and the contact surface. A slurry of the seed crystal is then transferred through the outlet 104 of the nucleation chamber 102 where it may be recovered or transferred to a downstream component (e.g., a crystallizer for controlling growth of the nuclei). The slurry may be transferred through the outlet via a fluid transfer device 115 that is positioned downstream of the outlet, for example.

It should be appreciated that flow of the feed solution into the nucleation chamber 102 and flow of the slurry out from the nucleation chamber 102 may be accomplished through the use of a fluid transfer device 113 upstream of the nucleation chamber 102, a fluid transfer device 115 downstream of the nucleation chamber 102 or both, in some embodiments. In some embodiments, flow of the feed solution into the nucleation chamber 102 and flow of the slurry out from the nucleation chamber 102 may be achieved by drawing the slurry out from the nucleation chamber 102 by creating a vacuum downstream of the outlet 104. In other embodiments, flow of the feed solution into the nucleation chamber and flow of the slurry out from the nucleation chamber 102 may be achieved by force of gravity, for example, where the storage container 114 is at an elevated position upstream from the nucleation chamber 102 inlet 103 and outlet 104.

It should also be appreciated that operation of the nucleation device 100 may be achieved through the use of one or more controllers that control various parameters of the process. Parameters that may be controlled, in some embodiments, include, for example, flow rate of the feed solution into the nucleation chamber 102, temperature of the fluid in the nucleation chamber 102, operation of the motive device 107, magnitude of the force applied between the parent crystal 105 and contact surface 108, extent of saturation of the feed solution and so on. The concentration of feed solution, in some embodiments, is maintained such that the process remains within the metastable zone width. A controller may employ any suitable control algorithms. The controller, for example, may be fully automatic, operating under program control in response to inputs (e.g., pressure, temperature, flow, force inputs) from various sensors or the like. In some embodiments, the controller may respond partially or solely to command inputs provided by a user. In embodiments in which the controller receives command inputs, those inputs may be received wirelessly, such as from a remote control, or may be received through a wired connection from a user interface element. In some embodiments in which the controller is fully automatic, the controller may include a processor, such as a microprocessor or a microcontroller, that executes a control algorithm encoded in software.

The process of nucleation and the size of the seed crystals (nuclei) produced in the process may be modulated, in part, by controlling the residence time of the supersaturated solution in the nucleation chamber. In some embodiments, residence time is determined by the volumetric capacity of the nucleation chamber and the rate of flow of the fluid through the chamber. Accordingly, the residence time can be controlled by controlling the rate of fluid flow, e.g., by controlling operation of fluid transfer devices positioned upstream and/or downstream from the nucleation chamber.

In some embodiments, nuclei generated using a nucleator exit the nucleator in a crystal slurry that can be directed to a downstream crystallizer (such as a tubular crystallizer or flow reactor-type crystallizer, e.g., a Coflore crystallizer) for further growth of nuclei into larger sizes. In some embodiments, integrated nucleator-crystallizer devices are provided in which nucleation and growth of crystals are decoupled, with nucleation occurring primarily in the nucleator and growth occurring primarily in the crystallizer, thus allowing advantageous control of the final crystal characteristics.

In some embodiments, nucleators are provided that are useful as continuous nucleation devices that may be connected directly to a downstream crystallizer where further growth of nuclei occurs. In some embodiments, integration of nucleators and crystallizers provides a platform in which nucleation and growth of crystals are decoupled, occurring primarily as individual events in separate vessels. In some embodiments, decoupling enables additional control over the crystallization process by permitting specific control over the extent of growth of nuclei. In some embodiments, an integrated nucleator-crystallizer device is provided that is useful for producing relatively small crystals (e.g., crystals of approximately 4 to 20 µm in mean Feret diameter or mean chord length (e.g., ~12 µm in mean Feret diameter or mean chord length)). In such embodiments, the integrated nucleator-crystallizer device may avoid the need of downstream post crystallization processes for producing populations of crystals of relatively uniformly small sizes.

Figure 1B:
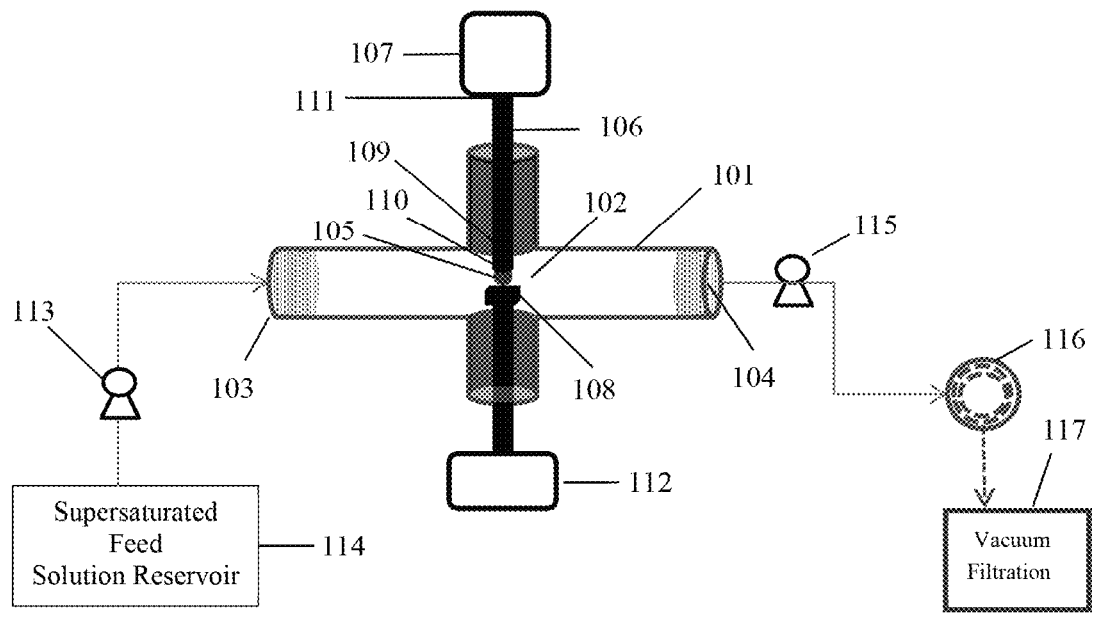
Figure 1C:
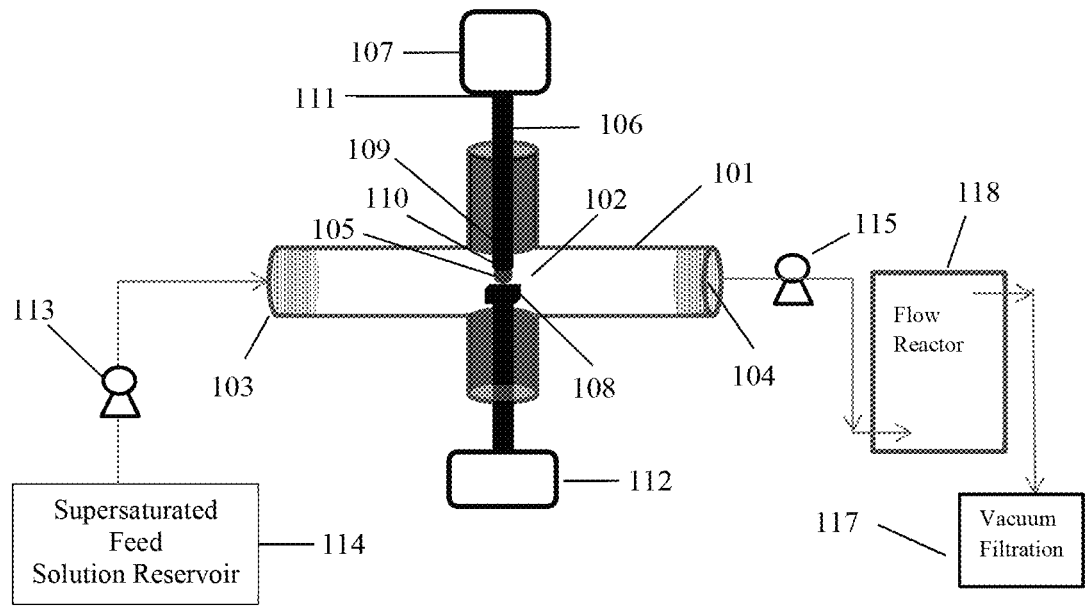

In some embodiments, as depicted in FIGS. 1B and 1C, outlet of a nucleation device 100 may be fluidically connected with a crystallizer chamber configured for containing a solution comprising nuclei (as a slurry) produced in the nucleation chamber under conditions that promote growth of the nuclei, thereby creating an integrated nucleator-crystallizer. In some embodiments, a process for operating the integrated nucleator-crystallizer involves nuclei generated in the nucleator being transferred (e.g., pumped) into the crystallization chamber, e.g., at the same flow rate as the they pass through the nucleator. The crystallization chamber may be a plug-flow crystallizer, a stirred tank crystallizer, a tubular crystallizer, a flow-reactor crystallizer, or a microfluidic crystallizer, for example. The small crystals then grow in the crystallizer for a defined and controllable residence time before the crystals are collected, for example by vacuum filtration 117, as shown in FIGS. 1B and 1C. In FIG. 1B, crystallization takes place in a tubular chamber 116 downstream of the nucleation device 100. Tubular chambers are well known in the art and may be obtained from commercial sources. For example, Masterflex® L/S®, Chem-Durance® Biotubing, e.g., size #16, (from Cole-Parmer, Vernon Hills, Ill.) may be used to create a tubular chamber that serves as a crystallizer for growing nuclei produced in the nucleation device 100.

In FIG. 1C, crystallization takes place in a flow reactor-type chamber 118 downstream of the nucleation device 100. The flow reactor is utilized as a downstream crystallizer for growing nuclei produced in the nucleation device to a desired size. Flow reactor chambers are also well known in the art and may be obtained from commercial sources. Coflore ACR—100 (AM Technology, Warrington, England) is an example of a commercially available flow reactor and other similar reactors are known in the art. The flow reactor chamber, in some embodiments, comprises a multicell reactor block (e.g., a Coflore ACR—100 reactor, AM Technology, Cheshire, UK) that uses dynamic mixing of a constituent fluid by means of shaking. In some embodiments, the device has multiple cells to prevent back flow of fluid during conditions of dynamic mixing. In some embodiments, the slurry is pumped into a first cell of the reactor and passes through the device from cell to cell via interconnecting channels at a predetermined flow rate. In some embodiments, the slurry is added directly to each well. The flow reactor may have up to 5, up to 10, up to 20, or more stages. The flow reactor may also be configured with one or more heating elements to control temperature of the flow reactor. The extent of crystal growth in the reactor is controlled at least in part by the retention time of the slurry in the reactor.

According to some aspects of the invention, the nucleation devices may, in some embodiments, be utilized for continuous or substantially continuous production of nuclei that are recovered and/or fed directly into a crystallizer for further growth of the nuclei. In some embodiments, the nucleation devices enable continuous crystallization processes aimed at obtaining populations of crystals of relatively narrow size distributions. In some embodiments, the nucleation devices enable continuous crystallization processes aimed at obtaining populations of crystals of relatively small size. In some embodiments, methods involve continuously feeding a crystallizer (e.g., a tubular chamber, a flow-reactor chamber) with crystals having a first characteristic size; maintaining the crystallizer under conditions suitable for crystal growth; and continuously recovering from the crystallizer crystals having a second characteristic size, wherein the difference between the first characteristic size and the second characteristic size is indicative of the extent of crystal growth in the crystallizer.

As used herein, the term "characteristic size" is a parameter that describes the physical dimensions of objects (e.g., crystals) in a population of the objects. In some embodiments, the characteristic size is determined by sampling a plurality of objects (e.g., crystals) in the population, obtaining a measurement indicative of the physical dimensions of the objects in the sample, and determining a summary statistic for the population based on the measurements obtained of the sample population. The measurement indicative of the physical dimension of the object may be a measure of size and/or shape in two or three dimensions. For example, the measurement may be a Feret diameter (e.g., average Feret diameter), a cross-sectional diameter, an equivalent circle diameter, an equivalent sphere diameter, an convex hull perimeter, circularity, convexity, extent of elongation, etc. The summary statistic may be mean, median, mode, standard deviation, variance, coefficient of variation, skewness, kurtosis, D10, D90 percentiles, and so on. Any of appropriate summary statistics may serve as a characteristic size of a population.

In some embodiments, the characteristic size is a "Feret diameter" which is the distance between the two parallel planes or lines that are tangential to an object (e.g., crystal). In some embodiments, the measure may be applied to projections of a three-dimensional object on a two-dimensional (2D) plane. In such cases, the Feret diameter is the distance between two tangential parallel lines rather than planes. This measure may be used in the analysis of particle sizes, for example, in microscopy. A mean Feret diameter of an object (e.g., crystal) is the mean of a plurality of distances (e.g., 2, 3, 4, 5, 6, 7, 8, 9, 10, 100, 1000 or more distances), in which each distance in the plurality is the distance between two different parallel planes or parallel lines that are tangential to the object or projection of the object on a 2D plane.

In some embodiments, measurements may be made of objects in the population by obtaining a microscopic image of the objects and performing an image analysis (e.g., using Image J software) to determine the size of objects in the image.

In some embodiments, Focused Beam Reflectance Measurement (FBRM) or similar technique may be used to obtain characteristic size information. FBRM, in some embodiments, provides an ability to measure objects (e.g., crystals) in suspensions, e.g., at full process concentration, without the need for sample extraction and sample preparation. In some embodiments, FBRM method of measurement may be used which is based on a measurement of Chord Length Distribution that simultaneously tracks the rate and degree of change in particle count and mean chord length. As used herein, the term "chord length" refers to the length of a line segment passing across a portion of a projection of an object on a two-dimensional plane, and whose end points lie on the edge of the projection. The term "mean chord length" refers to the mean length of multiple chords, e.g., multiple randomly orientated chords. Methods for measuring mean particle count and mean chord length are well known in the art. See, e.g., Henk G. Merkus. *Particle Size Measurements: Fundamentals, Practice, Quality*. Section 6.3.2. pages 150-151. Copyright 2009 Springer Science+Business Media B.V., and references cited therein.

In some embodiments, the characteristic size of nuclei produced in a nucleator is a mean Feret diameter of up to 1 µm, up to 5 µm, up to 10 µm, up to 15 µm, up to 20 µm, or up to 25 µm. In some embodiments, the characteristic size of nuclei produced in a nucleator is a mean chord length of up to 1 µm, up to 5 µm, up to 10 µm, up to 15 µm, up to 20 µm, or up to 25 µm. In either case, such crystals, in some embodiments, may be continuously fed into a crystallizer. In some embodiments of the crystallization methods, the characteristic size of crystals (grown from the nuclei in a crystallizer) being continuously recovered from the crystallizer is a mean Feret diameter or mean chord length in a range of about 1 to 25 µm, about 5 to 50 µm, about 10 to 50 µm, about 15 to 75 µm, about 20 to 75 µm, about 25 to 75 µm, or about 25 to 100 µm. In some embodiments, the characteristic size of nuclei being continuously feed into the crystallizer is a mean Feret diameter or mean chord length that is in a range of 5% to 10%, 5% to 15%, 5% to 20%, 5% to 25%, 10% to 30%, 10% to 40%, 25% to 45%, 25% to 50%, 25% to 65%, or 35% to 75% of the mean Feret diameter or mean chord length of crystals (grown from the nuclei) being continuously recovered from the crystallizer.

In some embodiments, the characteristic size of nuclei produced in a nucleator is at least 90% of the crystals having an mean Feret diameter or mean chord length in a range of up to 5 µm, up to 10 µm, up to 15 µm, up to 20 µm, up to 25 µm, up to 30 µm, or up to 40 µm. Such crystals, in some embodiments, may be continuously fed into a crystallizer. In some embodiments of the continuous crystallization methods, the characteristic size of crystals (grown from the nuclei) being continuously recovered from the crystallizer is at least 90% of the crystals having an mean Feret diameter or mean chord length in a range of up to 10 µm, up to 15 µm, up to 20 µm, up to 25 µm, up to 30 µm, up to 40 µm or up to 80 µm.

Exemplary embodiments of the invention will be described in more detail by the following examples. These embodiments are exemplary of the invention, which one skilled in art will recognize is not limited to the exemplary embodiments.

EXAMPLES

Example 1

Material and Methods

The following materials and methods relate to Examples 2-5.

Materials

Compounds utilized in crystallization studies included: glycine (Alfa Aesar), and acetaminophen (Sigma Aldrich Chemicals).

Preparation of the Parent Crystal

Parent crystals were generated by either slow cooling crystallization or direct tablet compression (Gamlen Tablet Press, UK). In some embodiments, for fast growing crystals, single parent crystal (size ≥1000 µm) were generated by cooling a supersaturated solution slowly (−0.01 to −0.035° C./min). For example, to generate a glycine parent crystal, a 30% (w/w) solution was cooled from 65 to 5° C. at −0.012° C./min.

In some embodiments, such as for slow growing crystals, other methods may be used to produce parent crystals, particularly for producing crystals larger than 1000 µm. In this case, the parent crystals can be generated by tablet compression. For example, an acetaminophen tablet was prepared by compressing acetaminophen powder (100 mg) twice with a force of 400 N.

Analysis of Crystal Size

Crystal size was typically determined by microscopy analysis. Microscopy analysis was generally performed directly on an outlet solution (e.g., a solution obtained from a nucleator or crystallizer) or with the crystals isolated from other stages of the crystallization process. To perform the analysis, a drop of solution or 1 mg of crystals dispersed in a few drops of mineral oil was first imaged using a 5× objective. Then, the image was analyzed using image analysis software (NIS element, Nikon). Average ferret diameter was used as the measure of particle size.

Experimental Setup

Figure 1D:
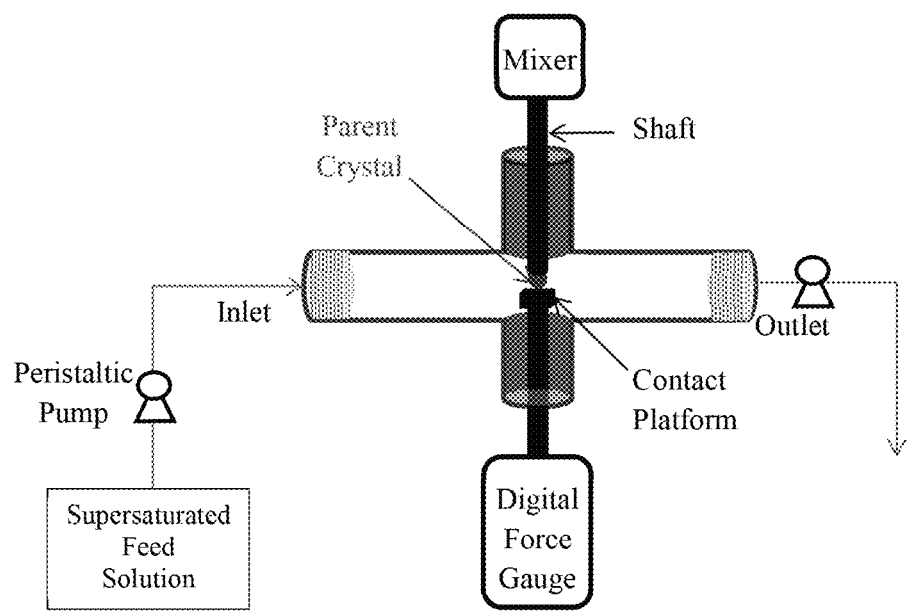

A schematic diagram of a nucleator is shown in FIG. 1D. The device consisted of three major components: (1) a "crossed" flow tube with four openings; (2) a parent crystal glued to the tip of a mixer shaft; and (3) a contact platform attached to a digital force gauge. The flow path through the nucleator had an internal diameter of about 15 mm, a length of about 60 mm, and total volume of about 8.6 mL.

During the crystallization process, supersaturated solution was fed into the nucleator via a peristaltic pump (fluid transfer device). The flow rate was calculated according to the desired residence time in the nucleator, e.g., to achieve a residence time ($\tau$) of 30 s, the flow rate was set to 17.2 mL/min. The concentration of the feed solution ($C_i$) was selected such that the operation stayed in the metastable zone width. For example, for the crystallization of glycine at room temperature (25° C.), the suitable range of feed solution concentration was about 20.5-25% (w/w).

When the parent crystal was immersed in the supersaturated solution, contact nucleation was initiated by rotating the parent crystal on the contact platform under an applied compression stress. Without wishing to be bound by theory, it was postulated that contact (between parent crystal and platform) results in removal of an adsorbed solute layer surrounding the parent crystals, leading to the generation of secondary nuclei. Once generated, continuous fluid motion pushed the newly generated secondary nuclei towards the outlet of the flow tube.

In some embodiments, it was advantageous for the stirring speed and applied stress to be selected to avoid micro-abrasion or breakage of the parent crystal. In some embodiments, for glycine crystal, a stirring speed of 30-45 rpm and an compression force of less than 0.5 N were suitable. In some embodiments, nucleation rate was related to the impact energy or compression force. Using the nucleator, the magnitude of the applied force was controlled by the weight of the stainless steel mixer shaft. However, it can be adjusted by other means including, for example, by changing the material of the mixer shaft, coupling additional weights to the shaft, etc. During the crystallization process, the magnitude of the applied force was measured by the digital force gauge (Imada DS-2 Force Gauge). Experiments were conducted with a stainless steel shaft (Diameter=6 mm) rotating at 30 rpm that yielded a force of 0.5 N approximately.

Example 2

Nucleator Assessment

Figure 2:
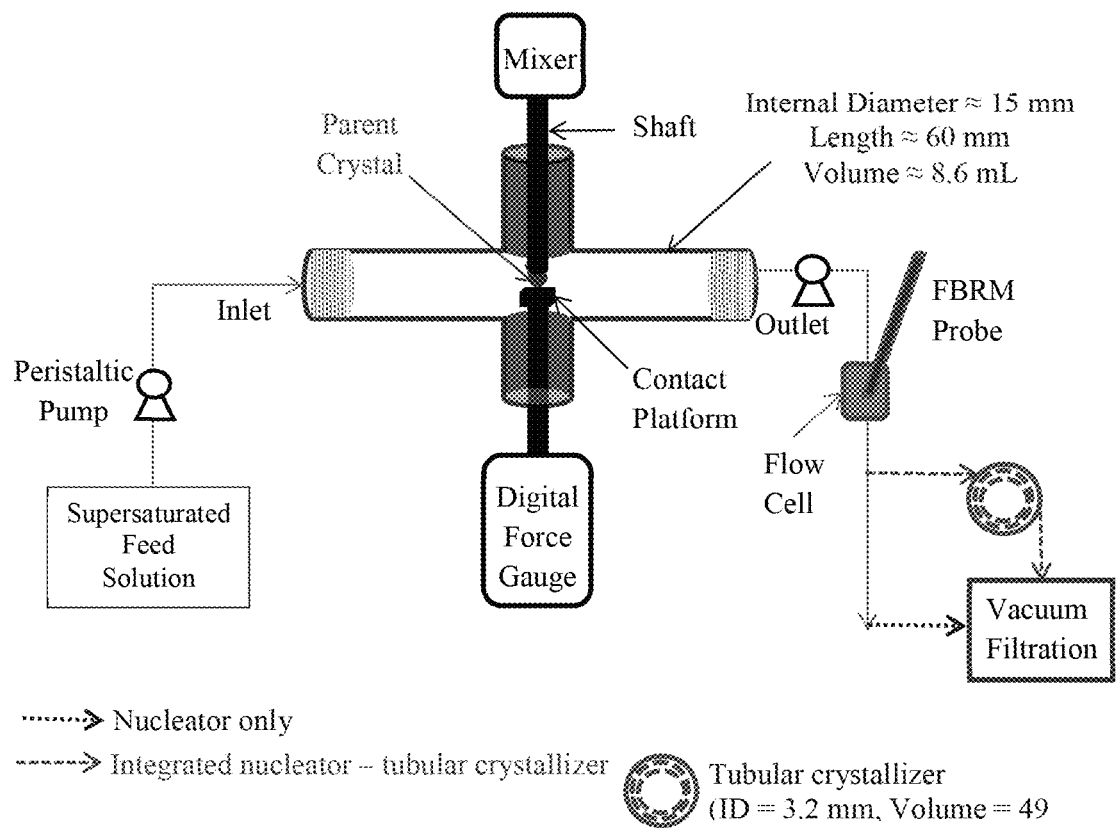
FIG. 2 is a schematic diagram of a nuclei generator (nucleator) and tubular crystallizer device (FBRM: Focused Beam Reflectance Measurement)

Nucleator experiments were conducted with glycine and acetaminophen, with a single crystal and a tablet as parent crystal, respectively. Experiments were conducted at room temperature (25° C.), where the concentrations of the feed solutions were held at 2.5-20% above saturation (Table 1). As shown in FIG. 2, two types of experiments were conducted. The first sets of experiment were conducted to evaluate the crystals generated by the nucleator, where crystals were immediately separated from the slurry via vacuum filtration (0.2 μm membrane) after four residence times. Experiments were conducted for glycine and acetaminophen, and the conditions are summarized in Table 1. In addition, to evaluate changes in the size distribution over the course of the experiment, an in-line FBRM® (G400, Mettler Toledo) probe was attached to the nucleator outlet for the acetaminophen experiments.

TABLE 1

Parameters for the nucleator only experiments
(w/w = g chemical/g solution)

| Chemicals | Feed solution Concentration (% w/w) | Saturation concentration at 25° C. ($C_s$) (% w/w) | Residence time, (s) |
|---|---|---|---|
| Glycine 25° C. | 20.5 | 20[15] | 120 |
|  | 21 |  | 30, 120, 210 |
|  | 24 |  | 10.3 |
| Acetaminophen 25° C. | 1.64 | 1.48[16] | 7.4, 10.3, 20.6 |

A second set of experiments were designed to demonstrate usefulness of the nuclei generator. These experiments involved connecting the generator to a tubular crystallizer for crystal growth. This integrated nucleator-crystallizer experiment was conducted with a 49 mL tubular coiled crystallizer (Masterflex® L/S®, Chem-Durance® Bio tubing, ID=3.2 mm, Length=20 ft) using 1.54% acetaminophen solution. During the experiment, relatively small crystals generated in the nucleator were pumped into the tubular crystallizer at the same flow rate as the nuclei generator. The small crystals then grew in the crystallizer for a fixed residence time before the crystals were collected by vacuum filtration, as shown in FIG. 2. Two experiments at flow rates of 14.2 and 11.3 mL/min were conducted. The particle size distributions of the crystals were determined by microscopic analysis (Nikon Eclipse ME600).

Figure 3:
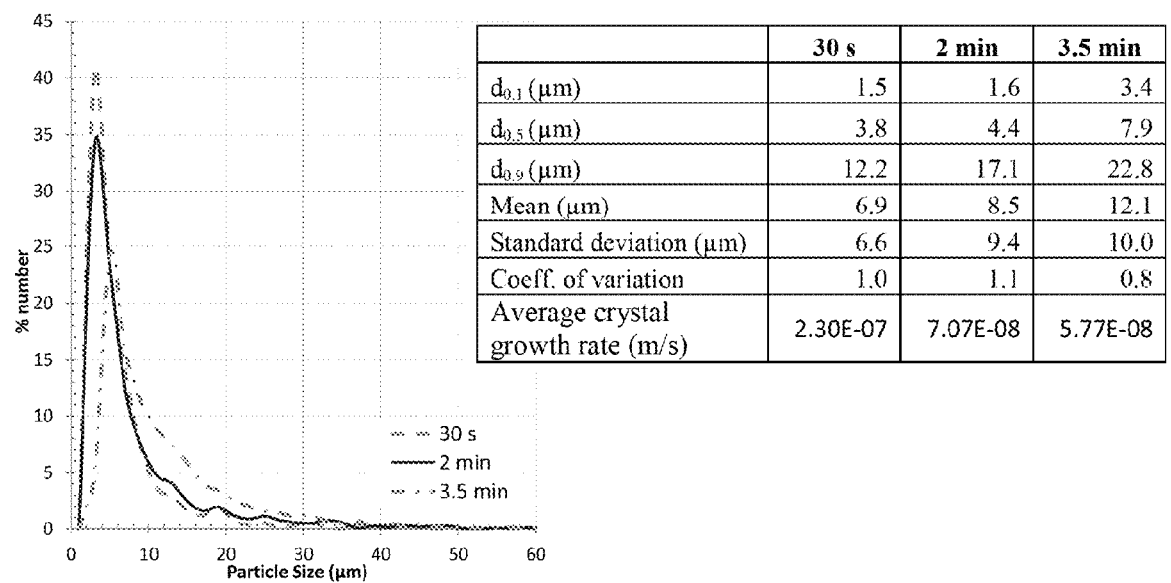
FIG. 3 depicts a size distribution plot of glycine crystals obtained from a nucleator experiment with 21% (w/w) feed solution at varying residence time (30 s, 2 min, 3.5 min)

To investigate the influence of residence time on the characteristics of secondary nucleation, three experiments with different residence times were conducted with the 21% glycine solution. The size distributions of the crystals obtained from these experiments are shown in FIG. 3. The nuclei obtained were mostly less than 20 μm with coefficient of variation (CV) of close to 1, e.g., 90% of the nuclei were less than 12.28 μm in a run with 30 s RT. In some embodiments, it was apparent from growth rates that the crystal growth was influenced by the rate of mass transfer. When the volumetric flow rate of the feed and outlet solution decreased with an increasing level of residence time, it resulted in a decrease in the rate of mass transfer, thus lowering the growth rate. These results indicated that the nuclei generator device (nucleator) was capable of producing nuclei of relatively small sizes with a relatively narrow size distribution using the principle of contact secondary nucleation. In addition, smaller crystals can be produced by reducing the residence time in the nucleator, and larger crystals can be produced by increasing the residence time.

Figure 4:
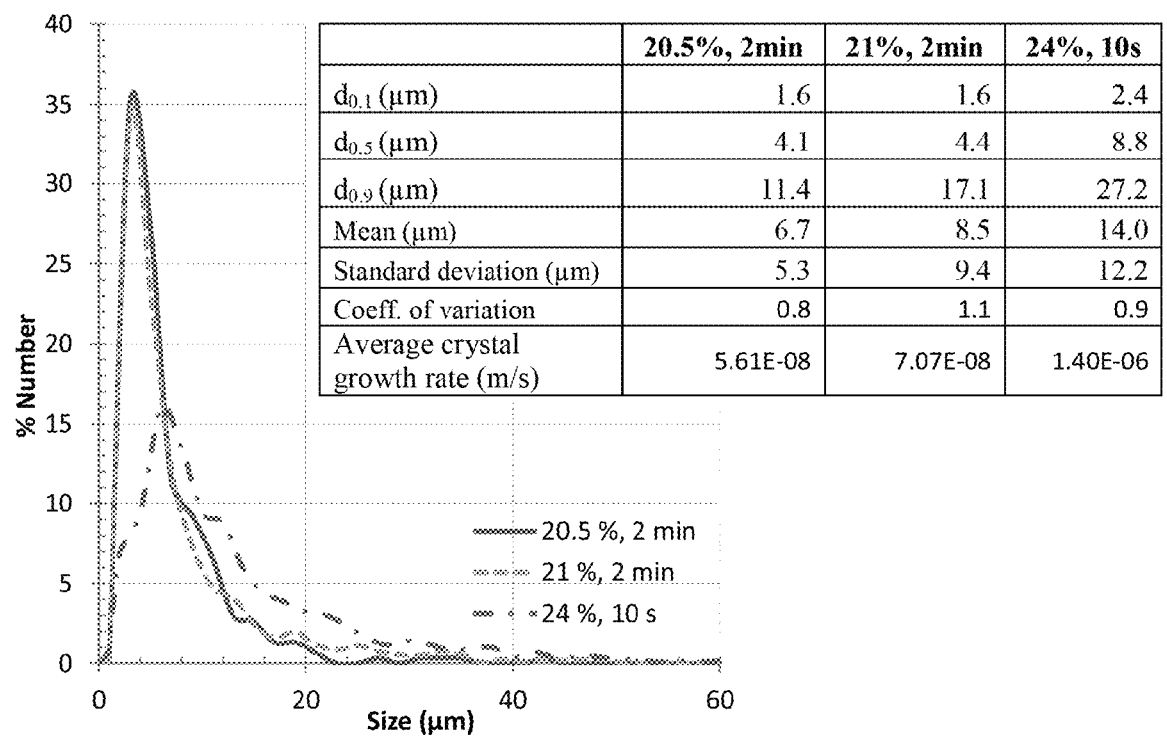
FIG. 4 shows distribution plots of glycine crystals obtained from a nucleator experiment with varying concentrations and residence times.
Figure 5A:
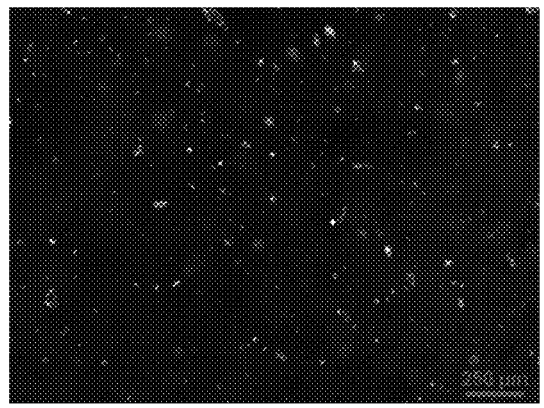
FIGS. 5A and 5B are polarized microscopic images of glycine crystal obtained from nucleator experiments with varying feed solution concentrations and 2 min residence time.
Figure 5B:
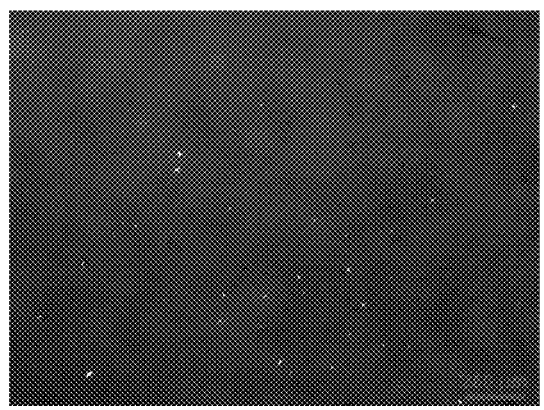

In addition to residence time, the degree of supersaturation is a parameter that influences the rate of nucleation, in some embodiments. Three experiments with supersaturation of 2.5%, 5% and 20% above saturation concentration ($C_s$) were conducted at varying residence time to assess the influence of the degree of supersaturation on the rate of nucleation. The size distributions and microscopic images are shown in FIGS. 4 and 5A-B. With the same RT, the size distribution of crystals obtained from 20.5 and 21% feed solution concentrations are similar, with slightly larger nuclei produced from the 21% run. When the supersaturation increases (e.g., 24% or $1.2C_s$), the absorbed layer is thicker and the size of critical nucleus is smaller, thus resulting in a faster nucleation rate with larger number of nuclei.

A combined impact of supersaturation and residence time (RT) is illustrated from FIGS. 3A and 4. In the example depicted in FIG. 3, when the supersaturation is the same, shorter RT results in smaller crystals. However, in FIG. 4, a 1.14× increase in the feed solution concentration (24%) generated larger crystals even at significantly (12×) shorter RT compared to the "21% 2 min" Run. This is at least partly a result of the significant increase in the average growth rate following the higher supersaturation level. Therefore, fast production of small nuclei can be achieved (with RTs on the order of seconds) at higher supersaturation. These data show that a user can tailor the desired size distribution of the nuclei by modifying the feed solution concentration or the residence time, in some embodiments.

Figure 6:
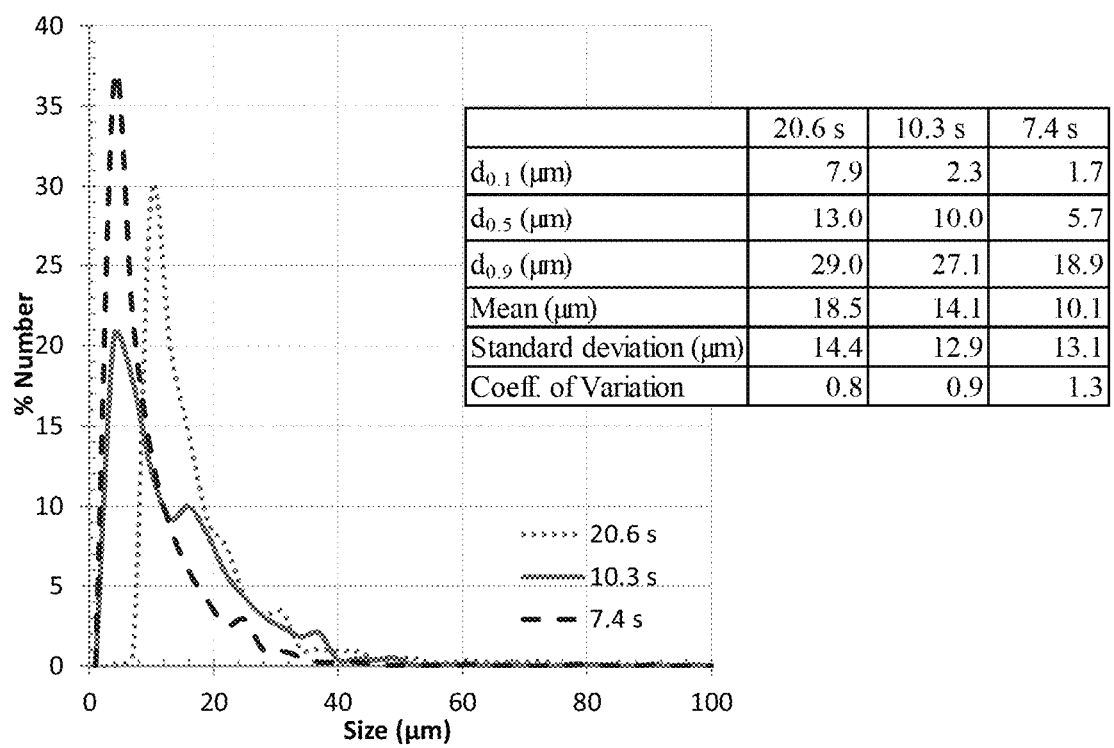
FIG. 6 shows size distribution plots of acetaminophen crystals at three different residence times.
Figure 7A:
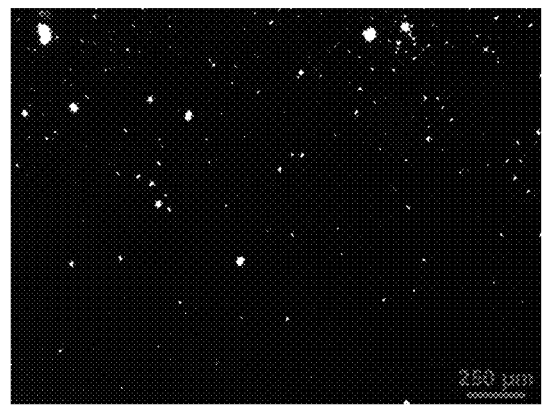
FIGS. 7A and 7B shows polarized microscopic images of acetaminophen crystals obtained from nucleator experiments at two different residence times (Scale bar: 50 μm)
Figure 7B:
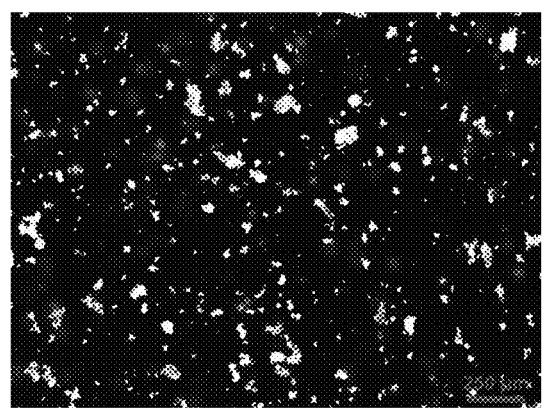

The glycine experiments showed that small crystals of mean size up to 14 μm were successfully generated with the nucleator device. In pharmaceutical manufacturing, a potential application is to use the nucleator to generate small active pharmaceutical ingredients (API) crystals directly, thereby avoiding or minimizing the need for post-processing prior to formulation into drug products. To illustrate this concept, experiments were conducted with acetaminophen, which is the active ingredient in many analgesic and antipyretic drugs. The parent acetaminophen crystal was generated by direct compression of acetaminophen. The first set of acetaminophen experiments was conducted with the nucleator (only) with residence times (RT) of 20.6 s, 10.3 s, and 7.4 s. Size distribution and microscopic images of the nuclei obtained are shown in FIGS. 6 and 7A-B. Similar to the observations in the glycine study, smaller nuclei are obtained from experiments with shorter RT. This example illustrates effectiveness of compressed tablet as a parent crystal.

Figure 8A:
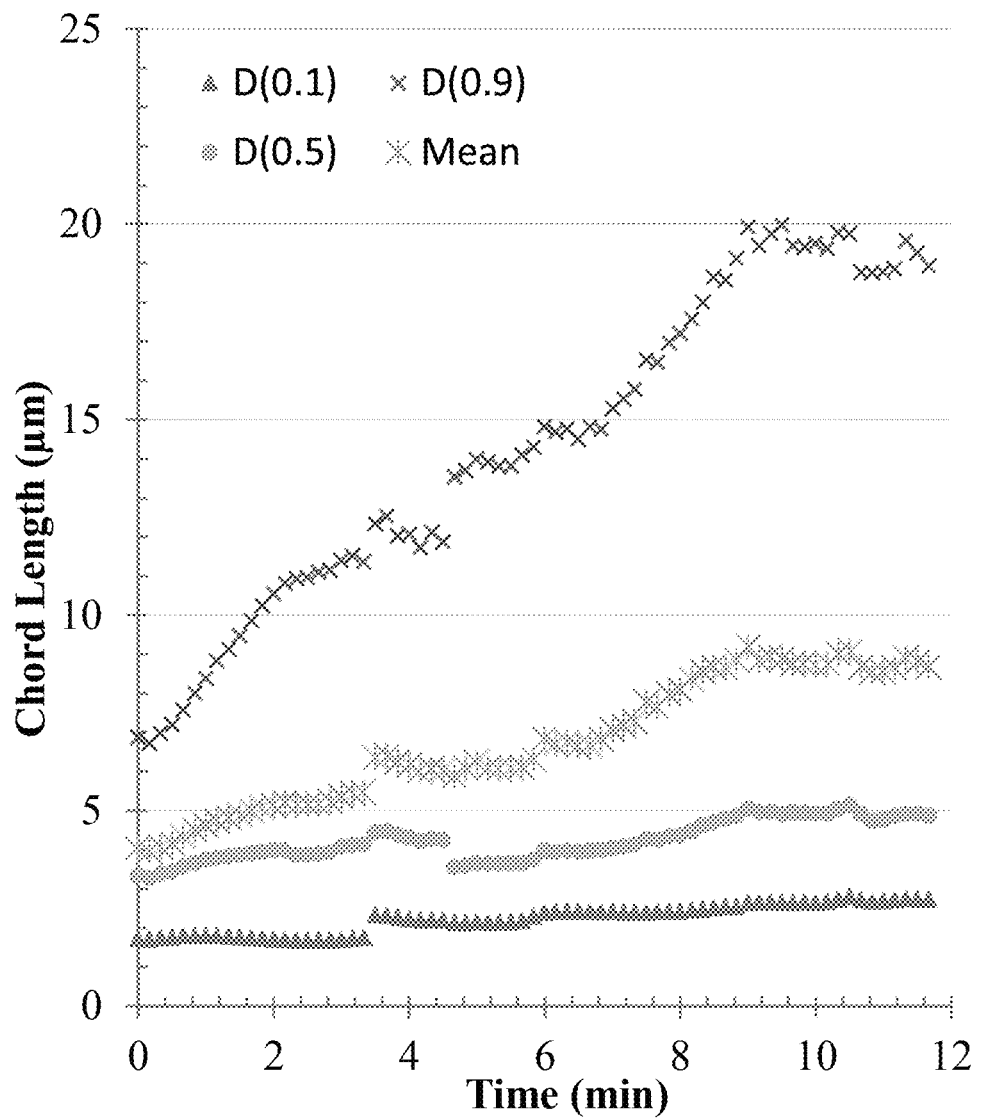
FIGS. 8A and 8B depict FBRM chord length statistics from the acetaminophen experiments with residence time of (A) 7.4 s (B) 10.3 s.
Figure 8B:
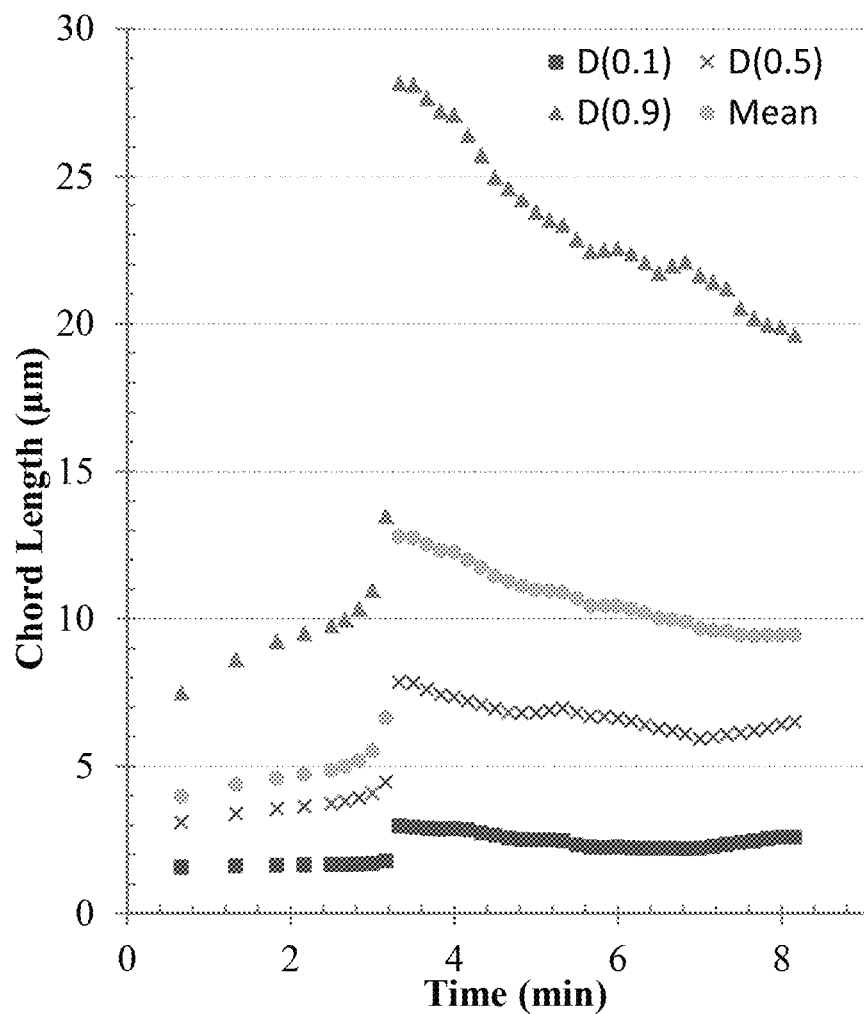

The statistics of the chord length distributions measured by the in-line FBRM probe are shown in FIGS. 8A-B. For both experiments, the size distributions stabilized after approx. 5-8 min, which is equivalent to 30-65 residence times. In both experiments, there were little changes in D (0.1) over time, which indicates that small crystals were constantly being generated. With nuclei generated by the nucleator being of the same approximate size, the span (D (0.9)-D (0.1)) of ≈20 μm indicates the presence of growth rate dispersion and residence time distributions inside the nucleator. Accordingly, some of the nuclei had grown to larger size while some of the population remains small, thereby contributed to the change in the D (0.9) over time. The FBRM monitoring data showed that the nucleator is capable of generating small crystals of desired mean size over a period of time, which is useful in continuous operations.

Example 3

Integrated Nucleator—Tubular Crystallizer

The nuclei generator can be integrated into crystallization processes in which the production of crystals of specific size distribution is desired (See, e.g., FIGS. 1B, 1C, 2, 12). In some embodiments, with the continuous generation of nuclei, the nucleation and growth events were decoupled. In this case, nucleation was triggered in the nucleator, while growth continued in the crystallizer. Multiple integrated nucleator—tubular crystallizer experiments were conducted that illustrate this process.

Figure 9:
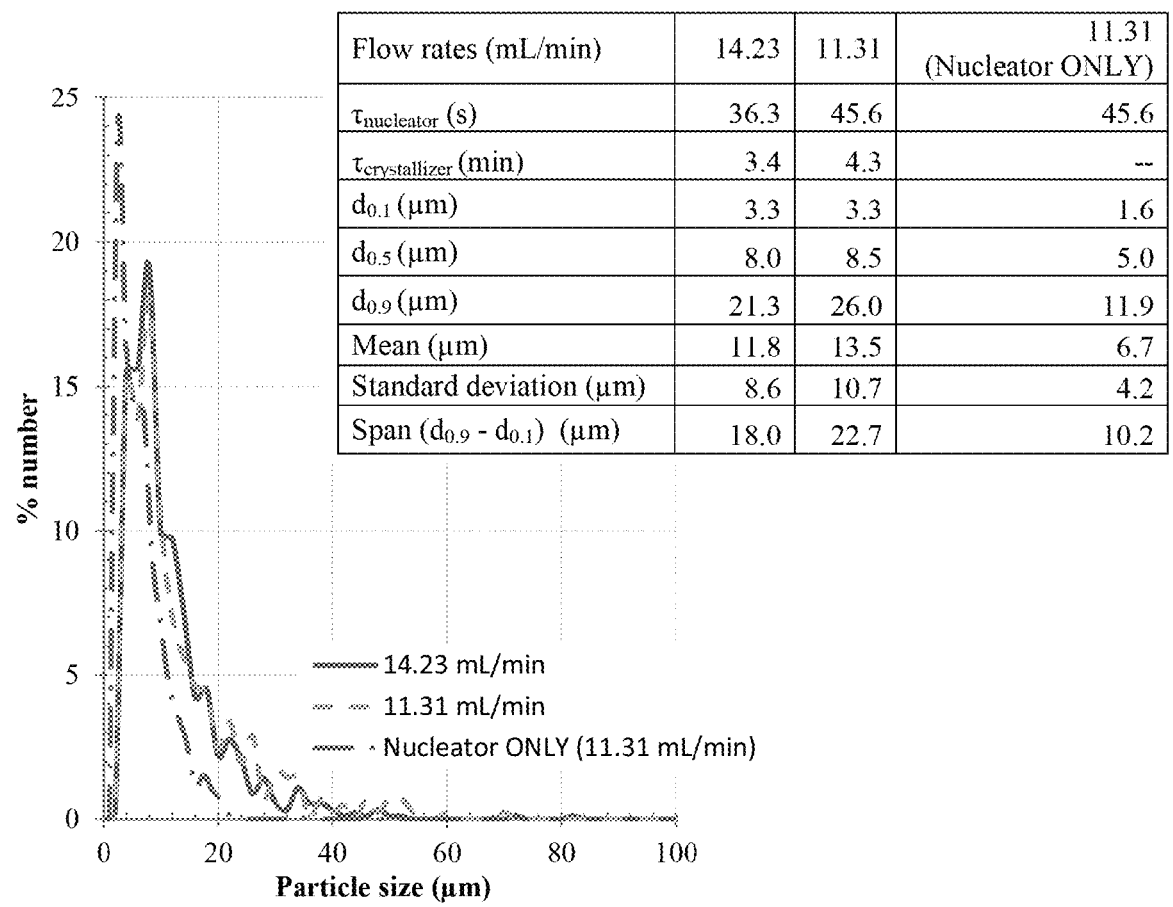
FIG. 9 shows crystal size distribution plots of an integrated nucleator-tubular crystallizer at two flow rates (τ: residence time)

FIG. 9 shows the size distribution of the acetaminophen crystals obtained from the integrated nucleator—tubular crystallizer experiments. With a fixed supersaturation, the mean size of the crystal can be controlled by the flow rates, which are essentially the residence time in the nucleator and crystallizer. Larger crystals with larger span and standard deviation are produced when the flow rate is lower (11.31 mL/min).

Also shown in FIG. 9 are results for the nucleator and integrated nucleator-crystallizer experiments at flow rate of 11.31 mL/min. The crystals left the nucleator with a mean size of 6.7 μm, after 4.3 min in the tubular crystallizer, the crystals had grown larger to a mean size of 13.5 μm. The acetaminophen crystals had average growth rates of $1.47 \times 10^{-7}$ m/s and $2.62 \times 10^{-7}$ m/s inside the nucleator and crystallizer, respectively. In this instance, the crystallization events were split into separate domains in which control of individual events was made possible: (1) the rate of nucleation and initial growth of nuclei was controlled by the feed concentration and residence time (flow rate) inside the nucleator; and (2) the growth rate of small crystals exiting the nucleator was controlled by the operating temperature and the length of the tubing (residence time). By decoupling the conditions for nucleation and growth, the crystallization process was advantageously controlled.

In the pharmaceutical industry, small crystals are often desired and are obtained through the use of post crystallization processes such as milling. In embodiments described herein that integrate nucleator and a tubular crystallizer, small acetaminophen crystals of mean size of 12 μm were readily produced, as shown in FIG. 9. Similar results can be obtained using other compounds. With this configuration, and similar configurations, crystals can be produced to the desired size range directly, eliminating additional post crystallization processes.

Example 4

Integrated Nucleator-Crystallizer (Coflore Crystallizer)

Figure 12:
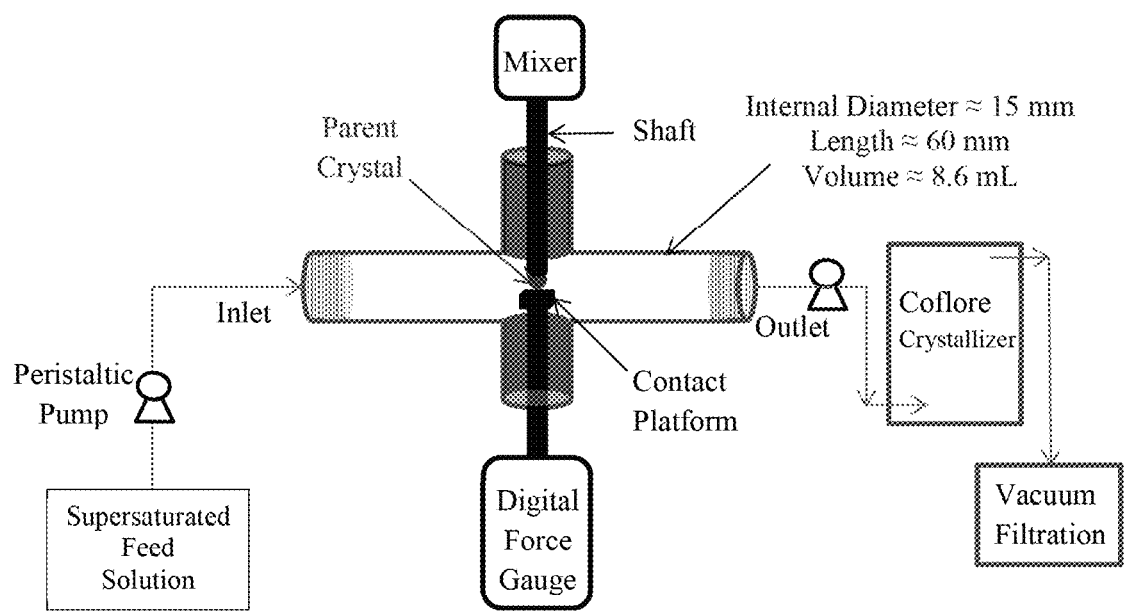
FIG. 12 is a schematic diagram of an integrated nucleator-crystallizer experiment.

An integrated nucleator-crystallizer was developed and utilized to produce glycine crystals. The device, as depicted in FIG. 12, utilized a CoFlore crystallizer. The device was operated with a seed solution concentration of approximately 24% (20% above saturation). The device was operated at a flow rate of 50 mL/min such that residence time in the nucleator was approximately 10 s and residence time in the crystallizer, which had a 100 mL total volume, was approximately 2 minutes. The crystallizer holding temperature was 28° C.

The size distribution and microscopic images of crystals collected from both nucleator and crystallizer (Coflore) are shown in FIGS. 10 and 11A-11B. The results showed that upon leaving the nucleator, the nuclei has an average size of 14 μm. The nuclei then grew to larger crystals with an average size of 48 μm. These results similarly indicated that with continuous generation of nuclei, the nucleation and growth events were essentially decoupled. In this case, nucleation was triggered in the nucleator, while growth is continued in the Coflore crystallizer.

The nucleator utilized herein is useful for generating uniformly sized crystals in continuous flow and can be used advantageously in place of conventional seeding practice used in batch crystallization processes. The results in Examples 3 and 4 illustrate that secondary nuclei generated (from the nucleator) can be pumped into the crystallizer directly, and grown into desired larger sizes in the crystallizers. The size of the secondary nuclei can be controlled by controlling the extent of supersaturation of the feed solution, magnitude of the applied force (e.g., compression, frictional) on the parent crystal, contact frequency (stirring speed), residence time (flow rate), etc. In addition, the device can be coupled to a micro- or mini-crystallizer thereby functioning as a seed crystal generation device. Uniformly sized nano-nuclei generated by this device can be used as a seed source, to produce uniformly sized nano or micro (<20 μm) crystals, and to prevent clogging of the flow channels.

The parent crystal used in this device was preserved (not destructed) over the processing time. Compared to conventional seeding practice that would consume seed materials, this device eliminated the need to prepare new seed materials.

Example 5

Figure 13:
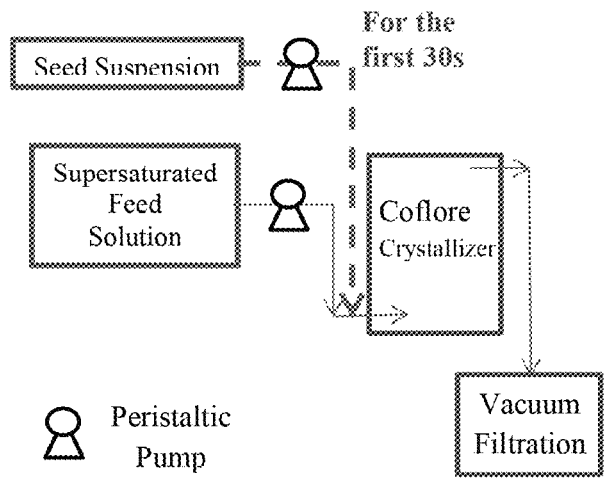
FIG. 13 is a schematic diagram of a seeded crystallization experiment.

Comparison of Integrated Nucleator-Crystallizer with a Continuous Crystallization Process with Batch Fed Seeding A continuous crystallization process with seeding was evaluated for comparison with an integrated nucleator-crystallizer device. A schematic diagram of the seeded crystallization experiment is depicted in FIG. 13. Seed crystals (nuclei) were obtained from antisolvent crystallization of glycine (to generate small crystals). Crystals obtained from antisolvent crystallization were sieved through a series of sieves with openings of 90, 63, and 45 μm. Seeds were collected from the 45 μm sieve.

For the seeded crystallization experiment, the crystallizer was first filled with the feed solution. Once filled, the process was seeded by pumping (50 mL/min) a suspension of 0.05 g seed in 25 mL feed solution into the crystallizer. After seeding, the crystallization process proceeded with continuous input of clear feed solution at 50 mL/min. Glycine crystals were collected by vacuum filtration at the crystallizer outlet. Except for the seeding procedure, the other experimental conditions for the seeded crystallization experiment were kept identical to the integrated nucleator-crystallizer experiment of Example 4.

Experiment Conditions for Seeded Crystallization Experiment for Glycine:
Feed solution concentration: 24% (20% above saturation)
Flow rate: 50 mL/min
Residence time in crystallizer (100 mL): 2 min
Crystallizer holding temperature: 28° C.

Results

Figure 14:
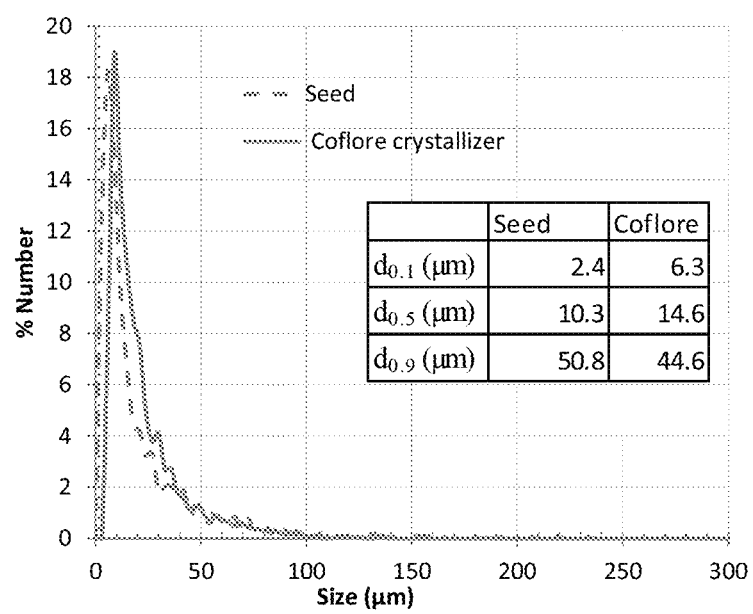
FIG. 14 shows crystal size distribution plots of glycine crystal obtained from a continuous crystallization process with seeding.

In a seeded crystallization operation, the seed crystal were generally washed out from the crystallizer within one or two residence times. The data were analyzed with crystals collected between 4-5 residence times (RT) when the device was at steady state. FIGS. 14 and 15A-15B shows that the crystal produced from the coflore crystallizer has similar size compared to the nuclei. Since the coflore crystallizer's crystals were collected between 4-5 RT, the crystals collected are crystals that nucleate and grow inside the crystallizer. The closed size distribution shows that in this configuration nucleation dominated in the coflore crystallizer, and the nuclei did not grow significantly.

To investigate the feasibility of the seeded experiment, a second experiment was conducted at lower crystallizer temperature (higher supersaturation that could potentially improve crystal growth rate). The size distributions are shown in FIG. 16. With higher supersaturation, the crystals produced from the coflore crystallizer still had a similar size distribution compared to the seed crystal. More crystals at higher size range (>50 μm) were detected. However, nucleation still dominated, and the growth rate was significantly smaller compared to that produced the integrated nucleator-crystallizer experiments.

For example, compared with FIGS. 10 and 11 that shows a distinct size distribution between crystals leaving the nucleator and crystallizer, FIGS. 14 and 15A-15B highlight the advantage of continuous seeding over the conventional approach. With continuous seeding (integrated nucleator-crystallizer), the nucleation and growth are decoupled. Nucleation dominates in the nucleator, while the nuclei continue to grow inside the crystallizer.

The size range of the crystals produced from the integrated nucleator-crystallizer and the seeded crystallization experiments are summarized in Table 2. The table shows that:
Smaller nuclei with narrower size distribution can be easily produced by the nucleator;
With a seeded crystallization process, it is possible to produce large crystal (Run 2). However, with coupled nucleation and growth inside the crystallizer, it may be difficult to control the deviation of size distribution. The decoupled integrated nucleator crystallization showed that crystals of narrower size range can be produced.

TABLE 2

Comparison of glycine crystals obtained from integrated nucleator-crystallizer experiment and conventional seeded crystallization process

| | Integrated nucleator crystallization | | Seeded Crystallization | |
|---|---|---|---|---|
| | | | Run 1 | Run 2 |
| | Nucleator | Coflore | Seed | ($T_{cryst}$ = 28° C.) | ($T_{cryst}$ = 25° C.) |
| $d_{0.1}$ (μm) | 2.4 | 13.9 | 2.4 | 6.3 | 7.4 |
| $d_{0.5}$ (μm) | 8.8 | 34.1 | 10.3 | 14.6 | 28.8 |
| $d_{0.9}$ (μm) | 27.2 | 91.9 | 50.8 | 44.6 | 90.3 |

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, and/or method described herein. In addition, any combination of two or more such features, systems, articles, materials, and/or methods, if such features, systems, articles, materials, and/or methods are not mutually inconsistent, is included within the scope of the present invention.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified unless clearly indicated to the contrary. Thus, as a non-limiting example, a reference to "A and/or B," when used in conjunction with open-ended language such as "comprising" can refer, in one embodiment, to A without B (optionally including elements other than B); in another embodiment, to B without A (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

Use of ordinal terms such as "first," "second," "third," etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

What is claimed is:

1. A device for nucleating crystals through contact secondary nucleation, the device comprising:
    a housing that comprises a nucleation chamber, a fluid inlet and a fluid outlet, the fluid inlet and fluid outlet each being in fluid communication with the nucleation chamber;
    a parent crystal connected to a support member within the nucleation chamber;
    a contact surface within the nucleation chamber that facilitates contact secondary nucleation through contact with the parent crystal in the presence of a supersaturated solution within the nucleation chamber; and
    a motive device operatively connected to the support member, wherein the motive device generates a mechanical force between the parent crystal and the contact surface to facilitate contact secondary nucleation.

2. The device of claim 1, wherein the device is configured such that, when a supersaturated solution comprising the same compounds that are constituents of the parent crystal is present in the nucleation chamber while the mechanical force is generated, a population of crystals comprising the compounds is produced in the nucleation chamber.

3. The device of any one of claims 1 to 2, wherein the parent crystal and the contact surface are configured such that a substantially normal force is exerted on the parent crystal through the contact surface.

4. The device of claim 1, wherein the motive device is configured for rotating the support member relative to the contact surface to produce a mechanical force between the parent crystal and a contact surface.

5. The device of claim 1, wherein the motive device is configured for translating the support member relative to the contact surface to produce a mechanical force between the parent crystal and a contact surface.

6. The device of claim 1 further comprising:
    a controller configured to automatically control the magnitude of the mechanical force by controlling operation of the motive device.

7. A device for processing crystals, the device comprising:
    (i.) a crystal nucleation device of claim 1;
    (ii.) a first container comprising a fluid outlet fluidically connected with the fluid inlet of the housing of the device;
    (iii.) a second container comprising a fluid inlet fluidically connected with the fluid outlet of the housing of the device; and
    (iv.) at least one fluid transfer device configured for transferring fluid from the first container through the nucleation chamber of the device to the second container.

8. A method comprising:
    obtaining device of claim 7;
    producing crystals in the crystal nucleation device;
    transferring the crystals to the second container; and
    growing the crystals in the second container.

9. The method of claim 8 further comprising:
causing the motive device to generate the mechanical force between the parent crystal and a contact surface to facilitate contact secondary nucleation within the nucleation chamber; and
transferring a solution to the nucleation chamber, wherein the solution comprises the same compounds that are constituents of the parent crystal that is present in the nucleation chamber, such that crystals comprising the compounds are produced in the nucleation chamber while the mechanical force is generated between the parent crystal and the contact surface.

* * * * *